US012648893B2

(12) United States Patent
Naftalovitz

(10) Patent No.:     US 12,648,893 B2
(45) **Date of Patent:         \*Jun. 9, 2026**

(54) VIAL ADAPTOR ASSEMBLY FOR A CLOSED FLUID TRANSFER SYSTEM

(71) Applicant: ELCAM MEDICAL A.C.A.L., Merom Hagalil (IL)

(72) Inventor: Ziv Naftalovitz, West Galilee (IL)

(73) Assignee: ELCAM MEDICAL A.C.A.L., Merom Hagalil (IL)

( \* ) Notice: Subject to any disclaimer, the term of this patent is extended or adjusted under 35 U.S.C. 154(b) by 335 days.

This patent is subject to a terminal disclaimer.

(21) Appl. No.: 18/075,532

(22) Filed: Dec. 6, 2022

(65) Prior Publication Data

US 2023/0124993 A1     Apr. 20, 2023

Related U.S. Application Data

(63) Continuation of application No. 16/763,365, filed as application No. PCT/IL2019/050003 on Jan. 2, 2019, now Pat. No. 11,571,362.

(Continued)

(51) Int. Cl.
| | |
|---|---|
| *A61J 1/14* | (2023.01) |
| *A61J 1/20* | (2006.01) |

(Continued)

(52) U.S. Cl.
CPC ........... *A61J 1/2096* (2013.01); *A61J 1/1406* (2013.01); *A61J 1/201* (2015.05); *A61J 1/2048* (2015.05);
(Continued)

(58) Field of Classification Search
CPC .. A61M 2005/3114; A61M 2005/3123; A61M 5/1782; B65B 3/003; A61J 1/1406;
(Continued)

(56) References Cited

U.S. PATENT DOCUMENTS 6,253,804 B1 \*   7/2001   Safabash ............... A61J 1/2096
                                                604/416
7,510,548 B2     3/2009   Seifert
                (Continued)

FOREIGN PATENT DOCUMENTS

AU       2016204189 A1     7/2016
AU       2017252789        11/2018
              (Continued)

*Primary Examiner* — Kai H Weng
(74) *Attorney, Agent, or Firm* — Sughrue Mion, PLLC

(57)                ABSTRACT

A vial adaptor assembly, suitable for use with a vial containing a medicament and a syringe adaptor, which is in turn connectable to a syringe having a piston adapted for selectable displacement in a first direction for drawing fluid into the syringe and in a second direction for expelling fluid from the syringe, the vial adaptor assembly including: a vial connector for non-removable connection with the vial containing a medicament: a syringe adaptor connector for connection with the syringe adaptor; a pressure equalization chamber having a variable volume, which is scaled from the outside environment during use; a liquid pathway communicating between an interior of the vial containing the medicament and an interior of the syringe when the syringe adaptor is connected to the syringe adaptor connector and the syringe is connected to the syringe adaptor and the vial connector is connected to the vial containing the medicament; and a venting pathway communicating between the interior of the vial containing the medicament and an interior of the pressure equalization chamber, when the vial connector is connected to the vial containing the medicament, wherein the pressure equalization chamber and the venting pathway are mutually configured such that, when the syringe adaptor is connected to the syringe adaptor connector and the syringe is connected to the syringe adaptor and the vial connector is connected to the vial containing the medicament, substantially all of any of the medicament that (Continued)

becomes located within the pressure equalization chamber is removed therefrom via the venting pathway and returned to the interior of the vial by displacement of the piston of the syringe in the first direction.

21 Claims, 34 Drawing Sheets

Related U.S. Application Data

(60) Provisional application No. 62/613,431, filed on Jan. 4, 2018.

(51) Int. Cl.
*A61M 5/178* (2006.01)
*A61M 5/31* (2006.01)

(52) U.S. Cl.
CPC .......... *A61J 1/2072* (2015.05); *A61M 5/1782* (2013.01); *A61M 2005/3114* (2013.01); *A61M 2005/3123* (2013.01)

(58) Field of Classification Search
CPC ........ A61J 1/201; A61J 1/2048; A61J 1/2055; A61J 1/2072; A61J 1/2096
See application file for complete search history.

(56) References Cited

U.S. PATENT DOCUMENTS

| | | | |
|---|---|---|---|
| 7,654,995 | B2 | 2/2010 | Seifert |
| 7,867,215 | B2 | 1/2011 | Aakerlund |
| 7,972,321 | B2 | 7/2011 | Fangrow |
| 8,206,367 | B2 | 6/2012 | Thomas |
| 8,475,404 | B2 | 7/2013 | Foshee |
| 8,512,307 | B2 | 8/2013 | Seifert |
| 8,540,692 | B2 | 9/2013 | Seifert |
| 8,827,977 | B2 | 9/2014 | Seifert |
| 8,827,978 | B2 | 9/2014 | Ellstroem |
| 8,864,725 | B2 | 10/2014 | Kent |
| 9,005,179 | B2 | 4/2015 | Seifert |
| 9,089,474 | B2 | 7/2015 | Cederschioeld |
| 9,107,808 | B2 | 8/2015 | Fangrow |
| 9,107,809 | B2 | 8/2015 | Lee |
| 9,132,062 | B2 | 9/2015 | Fangrow |
| 9,345,640 | B2 | 5/2016 | Peters |
| 9,351,906 | B2 | 5/2016 | Lee |
| 9,358,182 | B2 | 6/2016 | Lee |
| 9,364,396 | B2 | 6/2016 | Lee |
| 9,370,466 | B2 | 6/2016 | Lee |
| 9,381,137 | B2 | 7/2016 | Lee |
| 9,414,990 | B2 | 8/2016 | Craft |
| 9,597,260 | B2 | 3/2017 | Craft |
| 9,610,222 | B2 | 4/2017 | Kriheli |
| 9,662,272 | B2 | 5/2017 | Seifert |
| 9,701,427 | B2 | 7/2017 | Pierrick |
| 9,822,891 | B2 | 11/2017 | Cederschiold |
| 9,855,192 | B2 | 1/2018 | Cancellieri |

| | | | |
|---|---|---|---|
| 9,993,391 | B2 | 6/2018 | Fangrow |
| 9,999,570 | B2 | 6/2018 | Cancellieri |
| 10,022,302 | B2 | 7/2018 | Fangrow |
| 10,022,531 | B2 | 7/2018 | Shemesh |
| 10,071,020 | B2 | 9/2018 | Fangrow |
| 10,238,576 | B2 | 3/2019 | Lee |
| 10,299,990 | B2 | 5/2019 | Ben Shalom |
| 10,327,989 | B2 | 6/2019 | Fangrow |
| 10,327,992 | B2 | 6/2019 | Fangrow |
| 10,327,993 | B2 | 6/2019 | Fangrow |
| 10,398,627 | B2 | 9/2019 | Kriheli |
| 10,434,034 | B2 | 10/2019 | Cederschioeld |
| 10,478,382 | B2 | 11/2019 | Cederschiold |
| 10,517,797 | B2 | 12/2019 | Cancellieri |
| 10,619,752 | B2 | 4/2020 | Cederschiold |
| 10,682,505 | B2 | 6/2020 | Shemesh |
| 11,154,457 | B2 | 10/2021 | Cancellieri |
| 11,413,216 | B2 | 8/2022 | Mckinnon |
| 2007/0106244 | A1 | 5/2007 | Peters |
| 2008/0132854 | A1* | 6/2008 | Sharp .................... A61J 1/2096 604/240 |
| 2010/0218846 | A1 | 9/2010 | Kriheli |
| 2013/0228239 | A1* | 9/2013 | Cederschiold ........ A61J 1/2096 137/497 |
| 2015/0126974 | A1 | 5/2015 | Sanders |
| 2016/0206512 | A1 | 7/2016 | Chhikara |
| 2016/0250102 | A1 | 9/2016 | Lee |
| 2017/0333286 | A1 | 11/2017 | Phipps |
| 2018/0125759 | A1 | 5/2018 | Fangrow |
| 2018/0296440 | A1 | 10/2018 | Craft |
| 2019/0038506 | A1 | 2/2019 | Akerlund |
| 2019/0209434 | A1 | 7/2019 | Lee |
| 2019/0254926 | A1 | 8/2019 | Fangrow |
| 2020/0038292 | A1 | 2/2020 | Cederschiold |

FOREIGN PATENT DOCUMENTS

| | | | |
|---|---|---|---|
| EP | 1494748 | B1 | 1/2005 |
| EP | 1517663 | B1 | 6/2011 |
| EP | 2200559 | B1 | 11/2014 |
| EP | 2819633 | B1 | 6/2016 |
| EP | 2872101 | B1 | 9/2016 |
| EP | 2959877 | B1 | 3/2017 |
| EP | 2959879 | B1 | 3/2017 |
| EP | 2575734 | B1 | 4/2017 |
| EP | 2959878 | B1 | 4/2017 |
| EP | 2959880 | B1 | 4/2017 |
| EP | 2944302 | B1 | 6/2017 |
| EP | 2742925 | B1 | 8/2017 |
| EP | 3219354 | A2 | 9/2017 |
| EP | 3072494 | B1 | 10/2017 |
| EP | 3167866 | B1 | 11/2017 |
| EP | 3210588 | A3 | 12/2017 |
| EP | 3134057 | B1 | 6/2018 |
| EP | 3081204 | B1 | 5/2019 |
| EP | 3492061 | A1 | 6/2019 |
| EP | 3569217 | A1 | 11/2019 |
| EP | 3134059 | B1 | 3/2020 |
| EP | 3424824 | B1 | 3/2020 |
| WO | 2010/069359 | A1 | 6/2010 |
| WO | 2015/069654 | A1 | 5/2015 |

* cited by examiner

VIAL ADAPTOR ASSEMBLY FOR A CLOSED FLUID TRANSFER SYSTEM

REFERENCE TO RELATED APPLICATIONS

This application is a continuation of U.S. application Ser. No. 16/763,365, filed May 12, 2020, which is a National Stage of International Application No. PCT/IL2019/050003 filed Jan. 2, 2019, claiming priority based on U.S. Provisional Application No. 62/613,431 filed Jan. 4, 2018 and entitled "CLOSED FLUID TRANSFER SYSTEM", the disclosure of which is incorporated by reference in its entirety and priority of which is hereby claimed pursuant to 37 CFR 1.78(a) (4) and (5)(i).

FIELD OF THE INVENTION

The present disclosure relates generally to closed fluid transfer systems, and more specifically to a vial adaptor assembly enabling transfer of fluids between two containers while maintaining a closed system.

BACKGROUND OF THE INVENTION

Various types of vial adaptor assemblies for a closed fluid transfer systems are known in the art.

It is known that hazardous medicines are frequently applied in the treatment of certain medical conditions, however the use of such hazardous medicines presents danger to the health care providers. Accordingly, there is a need for a system that allows safe handling of hazardous medicines while reducing the exposure of health care providers and at the same time allows utilization of the entire amount of medicine contained in the system.

SUMMARY OF THE INVENTION

The present invention seeks to provide an improved vial adaptor assembly for a closed fluid transfer system and a method of use thereof.

There is thus provided in accordance with an embodiment of the present invention a vial adaptor assembly, suitable for use with a vial containing a medicament and a syringe adaptor, which is in turn connectable to a syringe having a piston adapted for selectable displacement in a first direction for drawing fluid into the syringe and in a second direction for expelling fluid from the syringe, the vial adaptor assembly including: a vial connector for non-removable connection with the vial containing a medicament; a syringe adaptor connector for connection with the syringe adaptor; a pressure equalization chamber having a variable volume, which is sealed from the outside environment during use; a liquid pathway communicating between an interior of the vial containing the medicament and an interior of the syringe when the syringe adaptor is connected to the syringe adaptor connector and the syringe is connected to the syringe adaptor and the vial connector is connected to the vial containing the medicament; and a venting pathway communicating between the interior of the vial containing the medicament and an interior of the pressure equalization chamber, when the vial connector is connected to the vial containing the medicament, wherein the pressure equalization chamber and the venting pathway are mutually configured such that, when the syringe adaptor is connected to the syringe adaptor connector and the syringe is connected to the syringe adaptor and the vial connector is connected to the vial containing the medicament, substantially all of any of the medicament that becomes located within the pressure equalization chamber is removed therefrom via the venting pathway and returned to the interior of the vial by displacement of the piston of the syringe in the first direction.

Preferably, the vial adaptor assembly also includes a deformable membrane, which is contained within a volume enclosed between the vial connector and the syringe adaptor connector and fixedly attached therebetween.

Further preferably, the pressure equalization chamber is disposed between the syringe adaptor connector and the deformable membrane. Still further preferably, the vial adaptor assembly also includes a needle element extending longitudinally along a longitudinal axis. Yet further preferably, the vial adaptor assembly also includes a septum element disposed within a portion of the syringe adaptor connector and configured for penetration thereof by a needle of a medical implement, which is adapted to engage the vial adaptor assembly. Still further preferably, the vial adaptor assembly also includes a plurality of circumferentially arranged snaps adapted for fixed engagement with the vial. Further preferably, the vial adaptor assembly also includes a sheath having an upper portion and a spike portion.

In accordance with an embodiment of the present invention, a longitudinal bore is formed through the sheath, and wherein the bore has a "drop" shape, having a wide portion and a narrow portion.

Preferably, a recess extends radially outwardly from the wide portion of the bore and is oppositely directed with respect to the narrow portion of the bore. Further preferably, an opening is formed in the spike portion and is adapted to communicate with the bore, the opening is oriented at the same direction as the recess. Still further preferably, the deformable membrane being a deformable sheet of material having a pre-defined shape, and which is adapted to change its shape in response to pressure that is applied thereon. Yet further preferably, the needle element has a cylindrical portion and a sharp tip and its inner volume defines the liquid pathway. Still further preferably, the needle element has a fin extending radially outwardly from the cylindrical portion and an opening formed in the cylindrical portion and adapted to communicate with the liquid pathway.

In accordance with an embodiment of the present invention, the opening is disposed adjacent the sharp tip of the needle element and is oriented at the same direction as the fin.

Preferably, a liquid medicament collecting and draining well is formed in the syringe adaptor connector, the liquid medicament collecting and draining well has it tapered wall surface and a flat surface. Further preferably, the pressure equalization chamber is formed between the deformable membrane and the syringe adaptor connector. Still further preferably, the deformable membrane is configured to change its shape in response to pressure that is exerted upon, thereby changing the volume of the pressure equalization chamber. Yet further preferably, the needle element is inserted into the wide portion of the bore, thus forming the venting pathway, which extends through the narrow portion of the bore. Still further preferably, the venting pathway at least partially surrounds the liquid pathway.

In accordance with an embodiment of the prevent invention, the fin is disposed within a portion of the sheath and is adapted to orient the needle element such that the opening of the needle element and the opening of the spike portion are facing the same direction.

Preferably, a tip of the needle element protrudes axially longitudinally from the spike portion and together therewith forms a sharp tip, which is adapted for penetrating a septum of the vial containing the medicament. Further preferably, increasing the pressure within the vial urges transfer of fluid from the vial into the pressure equalization chamber; and decreasing the pressure within the vial urges transfer of fluid from the pressure equalization chamber into the vial.

In accordance with an embodiment of the present invention, a method of communicating a medicament from a vial containing a medicament via a syringe adaptor to a syringe having a piston adapted for selectable displacement in a first direction for drawing fluid into the syringe and in a second direction for expelling fluid from the syringe, including; non-removably connecting a vial adaptor assembly to the vial containing a medicament and via the syringe adaptor to the syringe; displacing the piston in the first direction, thereby drawing a first quantity of the medicament into the syringe; thereafter displacing the piston in the second direction, thereby expelling at least a portion of the first quantity of the medicament into a pressure equalization chamber of the vial adaptor assembly, having a variable volume; and thereafter displacing the piston in the first direction, thereby expelling substantially all of the at least a portion of the first quantity of the medicament from the pressure equalization chandler of the vial adaptor assembly, into the vial.

Preferably, the vial adaptor assembly includes a vial connector for non-removable connection with the vial containing the medicament a syringe adaptor connector for connection with the syringe adaptor; a pressure equalization chamber having a variable volume, which is sealed from the outside environment during use. Further preferably, a liquid pathway communicating between an interior of the vial containing the medicament and an interior of the syringe when the syringe adaptor is connected to the syringe adaptor connector and the syringe is connected to the syringe adaptor and the vial connector is connected to the vial containing the medicament; and a venting pathway communicating between the interior of the vial containing the medicament and an interior of the pressure equalization chamber, when the vial connector is connected to the vial containing the medicament. Still further preferably, a liquid medicament collecting and draining well is formed in the syringe adaptor connector, the liquid medicament collecting and draining well has a tapered wall surface and a flat surface. Yet further preferably, a deformable membrane is fixedly retained between the vial connector and the syringe adaptor connector and the deformable membrane is configured to change its shape in response to pressure that is exerted upon, thereby changing the volume of the pressure equalization chamber. Further preferably, increasing the pressure within the vial urges transfer of fluid from the vial into the pressure equalization chamber; and decreasing the pressure within the vial urges transfer of fluid from the pressure equalization chamber into the vial.

In accordance with an embodiment of the present invention, a vial adaptor assembly, suitable for use with a vial containing a medicament and a syringe adaptor, which is in turn connectable to a syringe having a piston adapted for selectable displacement in a first direction for drawing fluid into the syringe and in a second direction for expelling fluid from the syringe, the vial adaptor assembly including; a vial connector for non-removable connection with the vial containing a medicament: a syringe adaptor connector for connection with the syringe adaptor; a pressure equalization chamber having a variable volume, which is sealed from the outside environment during use; a liquid pathway communicating between an interior of the vial containing the medicament and an interior of the syringe when the syringe adaptor is connected to the syringe adaptor connector and the syringe is connected to the syringe adaptor and the vial connector is connected to the vial containing the liquid medicament; and a venting pathway communicating between the interior of the vial containing the medicament and an interior of the pressure equalization chamber, when the vial connector is connected to the vial containing the medicament, and wherein the pressure equalization chamber is configured with a liquid medicament collecting and draining well communicating directly with the venting pathway.

Preferably, the vial adaptor assembly is generally axially symmetric about a longitudinal axis; the liquid pathway extends generally along the longitudinal axis; the venting pathway at least partially surrounds the liquid pathway; and the liquid medicament collecting and draining well is generally centered along the longitudinal axis. Further preferably, the pressure equalization chamber and the venting pathway are mutually configured such that, when the syringe adaptor is connected to the syringe adaptor connector and the syringe is connected to the syringe adaptor and the vial connector is connected to the vial containing the medicament, substantially all of any of the medicament that becomes located within the pressure equalization chamber is removed therefrom via the venting pathway and returned to the interior of the vial by displacement of the piston of the syringe in the first direction. Still further preferably, the vial adaptor assembly also includes a deformable membrane, which is contained within a volume enclosed between the vial connector and the syringe adaptor connector and fixedly attached therebetween. Yet further preferably, the pressure equalization chamber is disposed between the syringe adaptor connector and the deformable membrane.

In accordance with an embodiment of the present invention, the vial adaptor assembly also includes a needle element extending longitudinally along a longitudinal axis.

Preferably, the vial adaptor assembly also includes a septum element disposed within a portion of the syringe adaptor connector and configured for penetration thereof by a needle of a medical implement, which is adapted to engage the vial adaptor assembly. Further preferably, the vial connector also includes a plurality of circumferentially arranged snaps adapted for fixed engagement with the vial. Still further preferably, the vial connector also includes a sheath having an upper portion and a spike portion. Yet further preferably, a longitudinal bore is formed through the sheath, and wherein the bore has a "drop" shape, having a wide portion and a narrow portion.

In accordance with an embodiment of the present invention, a recess extends radially outwardly from the wide portion of the bore and is oppositely directed with respect to the narrow portion of the bore.

Preferably, an ripening is formed in the spike portion and is adapted to communicate with the bore, the opening is oriented at the same direction as the recess. Further preferably, the deformable membrane being a deformable sheet of material having a pre-defined shape, and which is adapted to change its shape in response to pressure that is applied thereon. Still further preferably, the needle element has a cylindrical portion and a sharp tip and its inner volume defines the liquid pathway. Yet further preferably, the needle element has a fin extending radially outwardly from the cylindrical portion and an opening formed in the cylindrical portion and adapted so communicate with the liquid pathway.

In accordance with an embodiment of the present invention, the opening is disposed adjacent the sharp tip of the needle element and is oriented at the same direction as the fin.

Preferably, the liquid medicament collecting and draining well has a tapered wall surface and a flat surface. Further preferably, the pressure equalization chamber is formed between the deformable membrane and the syringe adaptor connector. Still further preferably, the deformable membrane is configured to change its shape in response to pressure that is everted upon, thereby changing the volume of the pressure equalization chamber. Yet further preferably, the needle element is inserted into the wide portion of the bore, thus forming the venting pathway, which extends through the narrow portion of the bore.

In accordance with an embodiment of the present invention, the fin is disposed within a portion of the sheath and is adapted to orient the needle element such that the opening of the needle element and the opening of the spike portion are facing the same direction.

Preferably, a tip of the needle element protrudes axially longitudinally from the spike portion and together therewith forms a sharp tip, which is adapted for penetrating a septum of the vial containing the medicament. Further preferably, increasing the pressure within the vial urges transfer of fluid from the vial into the pressure equalization chamber; and decreasing the pressure within the vial urges transfer of fluid from the pressure equalization chamber into the vial.

In accordance with an embodiment of the present invention, a vial adaptor assembly, suitable for use with a vial containing a medicament and a syringe adaptor, which is in turn connectable to a syringe having a piston adapted for selectable displacement in a first direction for drawing fluid into the syringe and in a second direction for expelling fluid from the syringe, the vial adaptor assembly including: a vial connector for non-removable connection with the vial containing a medicament; a syringe adaptor connector for connection with the syringe adaptor; a pressure equalization chamber having a variable volume, which is sealed from the outside environment during use; a liquid pathway communicating between an interior of the vial containing the medicament and an interior of the syringe when the syringe adaptor is connected to the syringe adaptor connector and the syringe is connected to the syringe adaptor and the vial connector is connected to the vial containing the medicament; and a venting pathway communicating between the interior of the vial containing the medicament and an interior of the pressure equalization chamber, when the vial connector is connected to the vial containing the medicament, and wherein: the vial adaptor assembly is generally axially symmetric about a longitudinal axis; the liquid pathway extends generally along the longitudinal axis; and the venting pathway at least partially surrounds the liquid pathway.

Preferably, the pressure equalization chamber is configured with a liquid medicament collecting and draining well communicating directly with the venting pathway. Further preferably, the liquid medicament collecting and draining well is generally centered along the longitudinal axis. Still further preferably, the pressure equalization chamber and the venting pathway are mutually configured such that, when the syringe adaptor is connected to the syringe adaptor connector and the syringe is connected to the syringe adaptor and the vial connector is connected to the vial containing the medicament, substantially all of any of the medicament that becomes located within the pressure equalization chamber is removed therefrom via the venting pathway and returned to the interior of the vial by displacement of the piston of the syringe in the first direction. Yet further preferably, the vial adaptor assembly also includes a deformable membrane, which is contained within a volume enclosed between the vial connector and the syringe adaptor connector and fixedly attached therebetween.

In accordance with an embodiment of the present invention, the pressure equalization chamber is disposed between the syringe adaptor connector and the deformable membrane.

Preferably, the vial adaptor assembly also includes a needle element extending longitudinally along the longitudinal axis. Further preferably, the vial adaptor assembly also includes a septum element disposed within a portion of the syringe adaptor connector and configured for penetration thereof by a needle of a medical implement, which is adapted to engage the vial adaptor assembly. Yet further preferably, the vial connector also includes a plurality of circumferentially arranged snaps adapted for fixed engagement with the vial.

In accordance with an embodiment of the present invention, the vial connector also includes a sheath having an upper portion and a spike portion.

Preferably, a longitudinal bore is formed through the sheath, and wherein the bore has a "drop" shape, having a wide portion and a narrow portion. Further preferably, a recess extends radially outwardly from the wide portion of the bore and is oppositely directed with respect to the narrow portion of the bore. Still further preferably, an opening is formed in the spike portion and is adapted to communicate with the bore, the opening is oriented at the same direction as the recess. Yet further preferably, the deformable membrane being a deformable sheet of material having a predefined shape, and which is adapted to change its shape in response to pressure that is applied thereon.

In accordance with an embodiment of the present invention, the needle element has a cylindrical portion and a sharp tip and its inner volume defines the liquid pathway.

Preferably, the needle element has a fin extending radially outwardly from the cylindrical portion and an opening formed in the cylindrical portion and adapted to communicate with the liquid pathway. Further preferably, the opening is disposed adjacent the sharp tip of the needle element and is oriented at the same direction as the fin. Still further preferably, the liquid medicament collecting and draining well has a tapered wall surface and a flat surface. Yet further preferably, the pressure equalization chamber is formed between the deformable membrane and the syringe adaptor connector.

In accordance with an embodiment of the present invention, the deformable membrane is configured to change its shape in response to pressure that is exerted upon, thereby changing the volume of the pressure equalization chamber.

Preferably, the needle element is inserted into the wide portion of the bore, thus forming the venting pathway, which extends through the narrow portion of the bore. Further preferably, the fin is disposed within a portion of the sheath and is adapted to orient the needle element such that the opening of the needle element and the opening of the spike portion are facing the same direction. Still further preferably, a tip of the needle element protrudes axially longitudinally from the spike portion and together therewith forms a sharp tip, which is adapted for penetrating a septum of the vial containing the medicament. Yet further preferably, increasing the pressure within the vial urges transfer of fluid from the vial into the pressure equalization chamber; and decreasing the pressure within the vial urges transfer of fluid from the pressure equalization chamber into the vial.

BRIEF DESCRIPTION OF THE DRAWINGS

The present invention will be understood and appreciated more fully from the following detailed description, taken in conjunction with the drawings in which:

7

Figure 1:
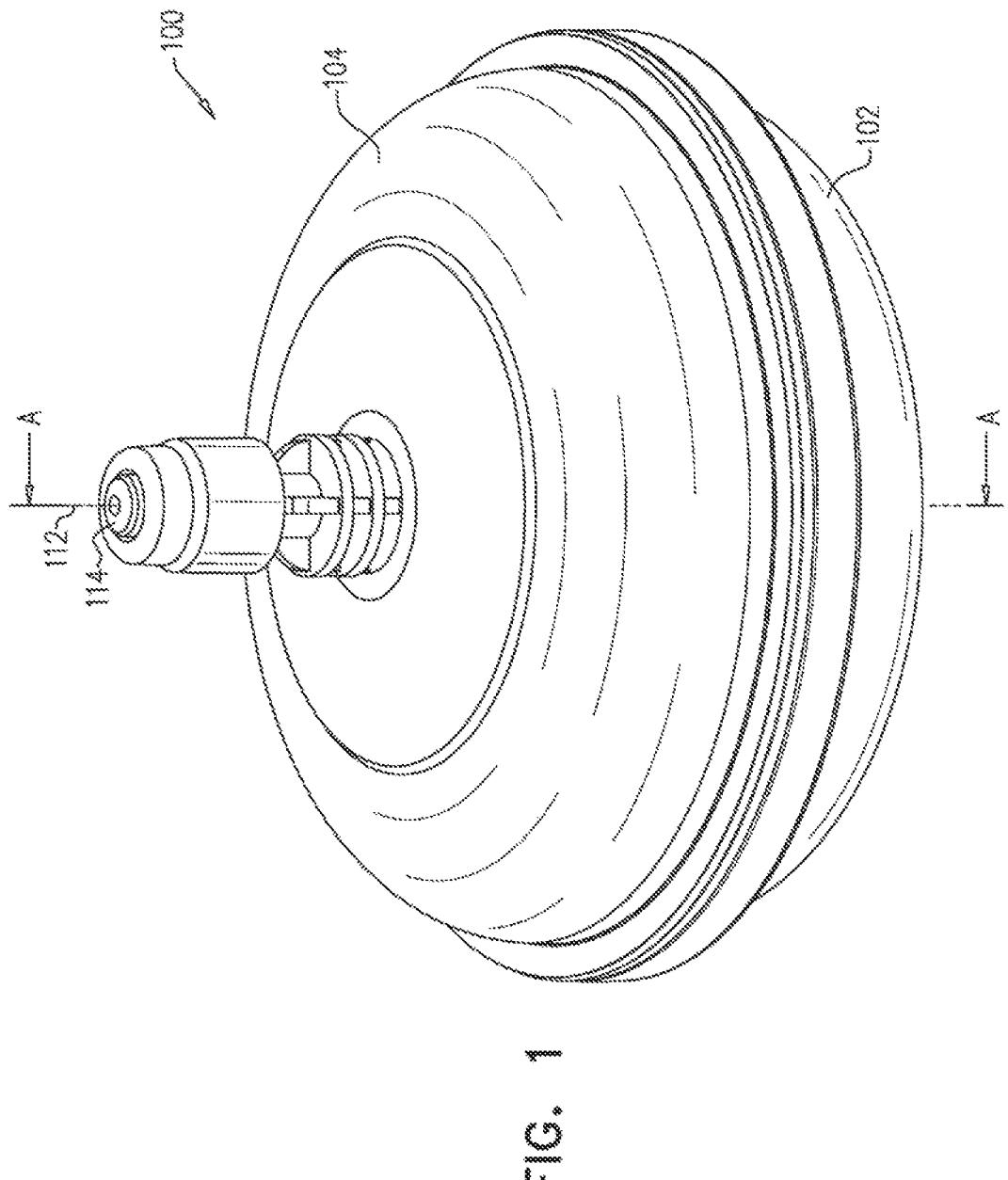
Figure 2:
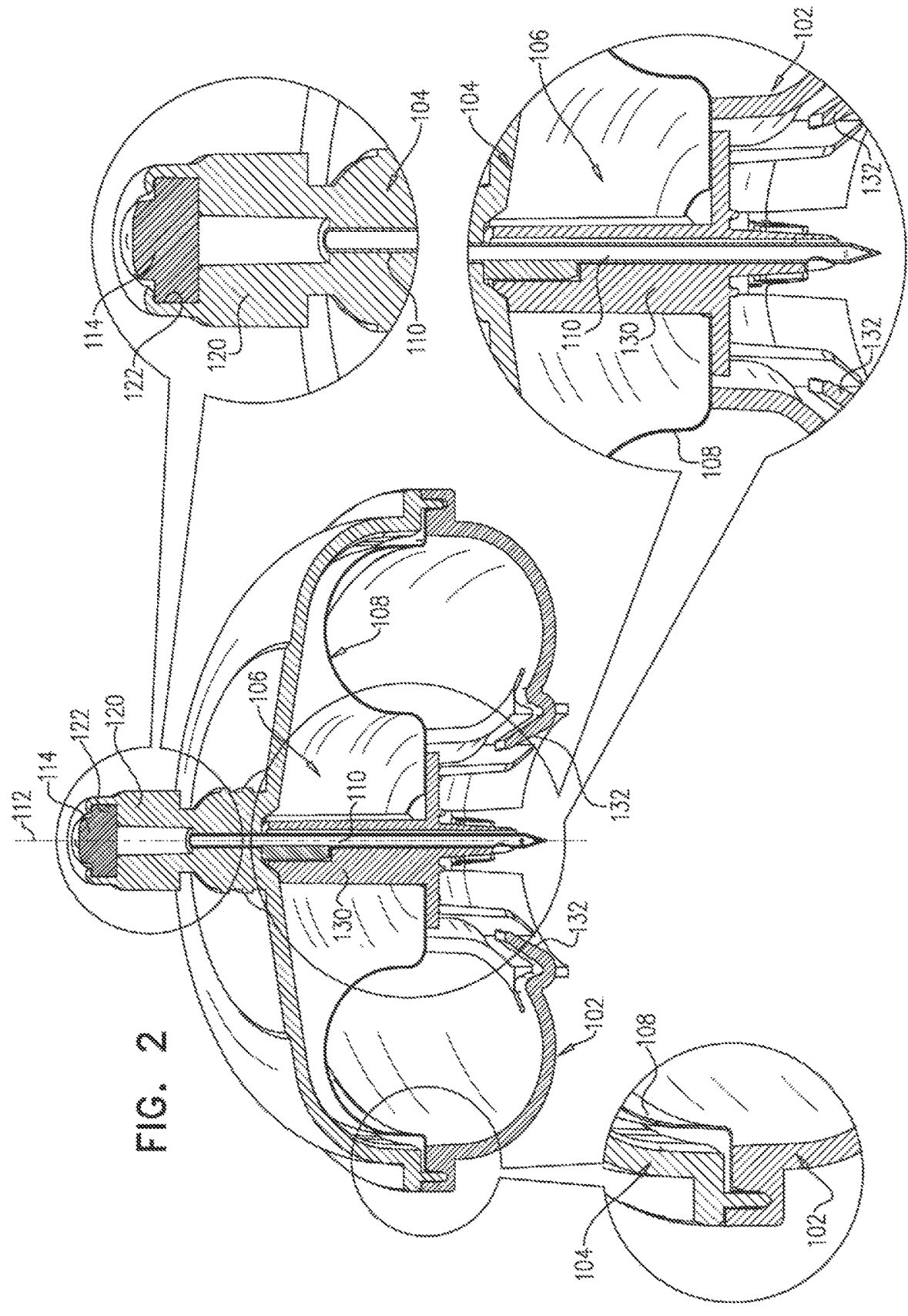
Figure 3A:
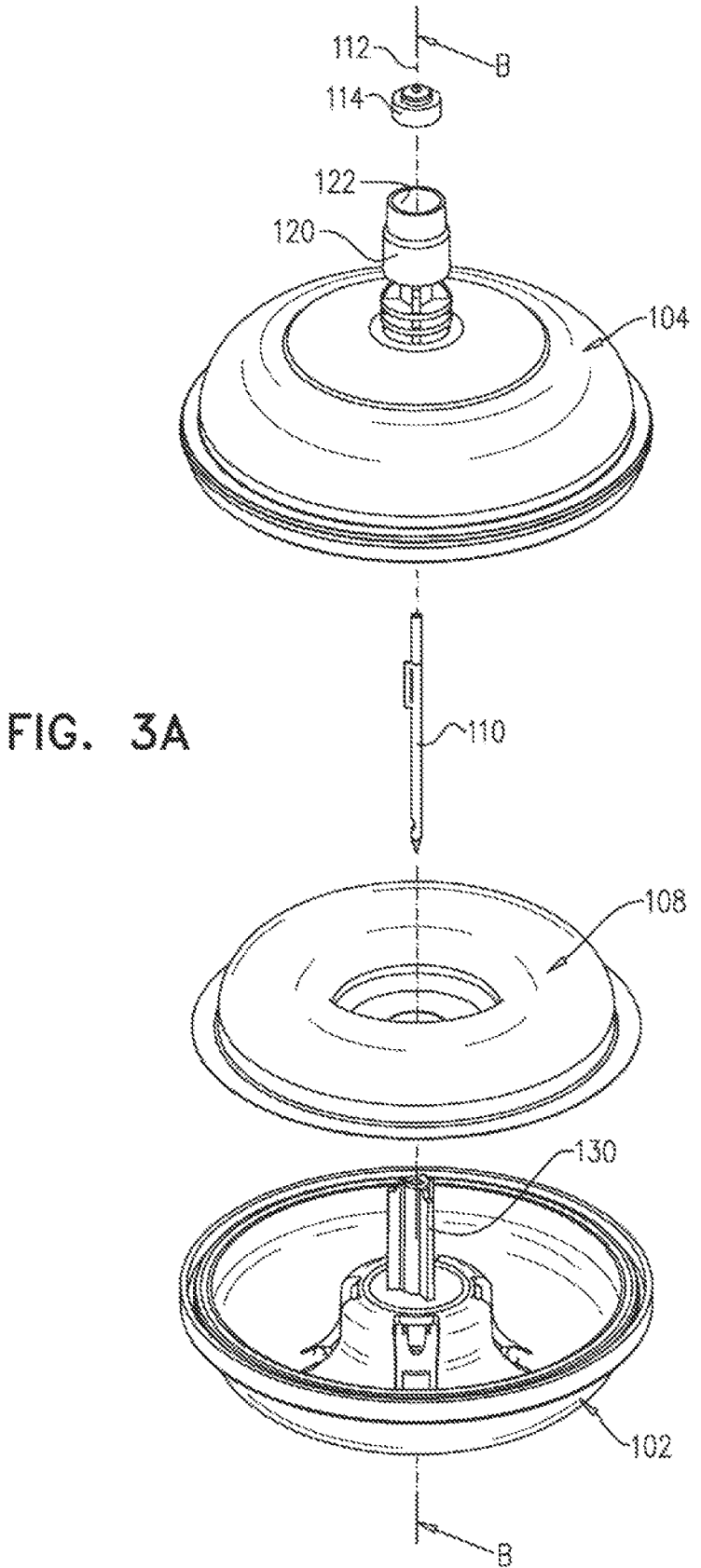
Figure 3B:
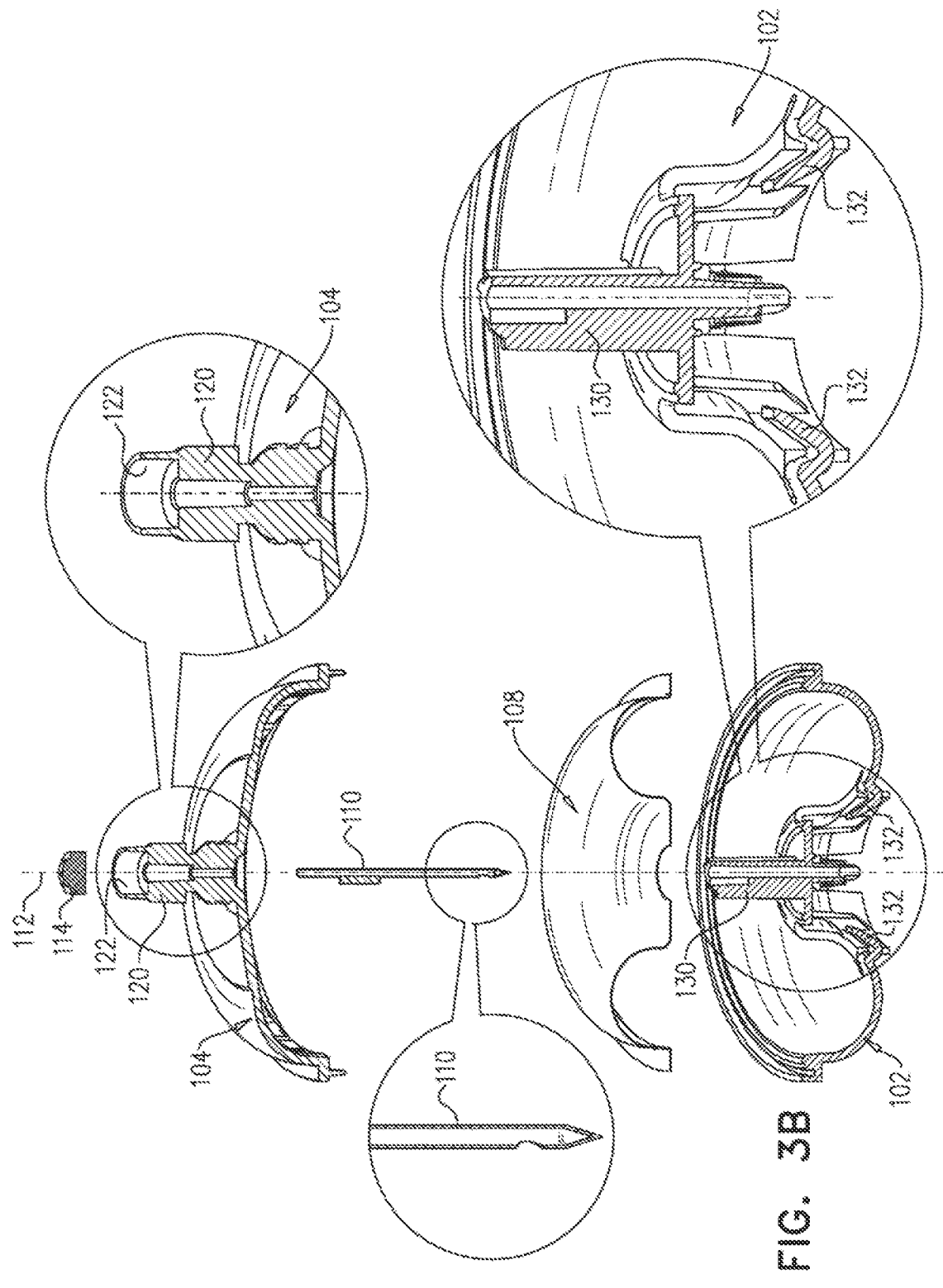
Figure 4A:
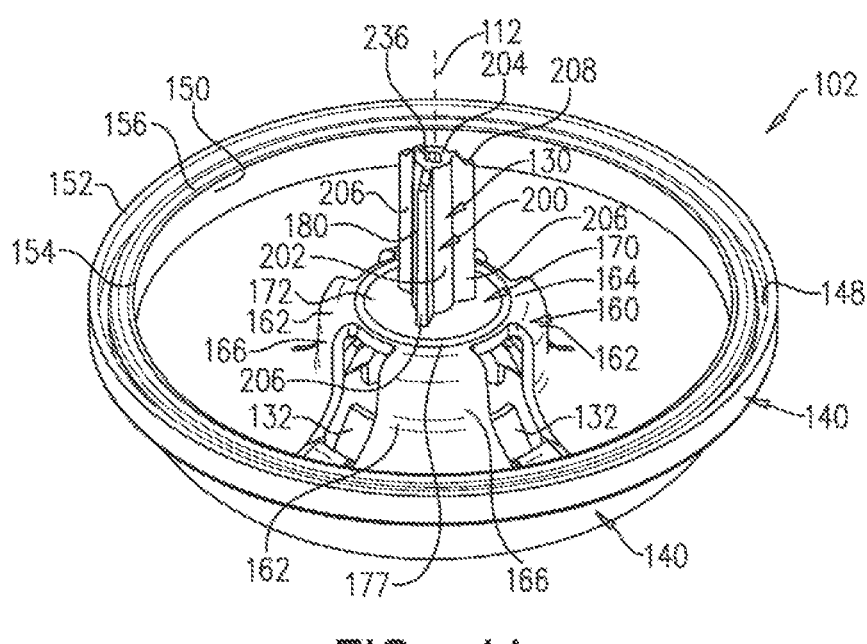
Figure 4B:
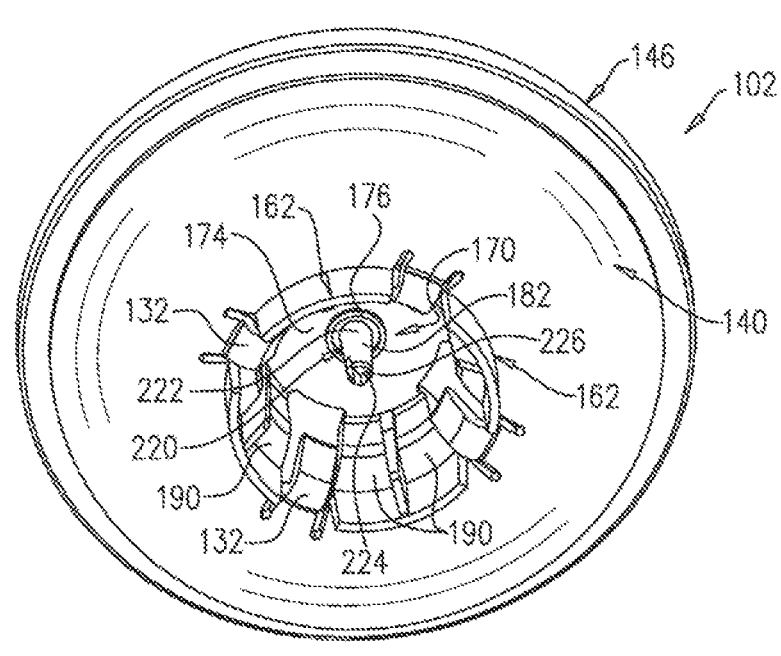
Figure 4C:
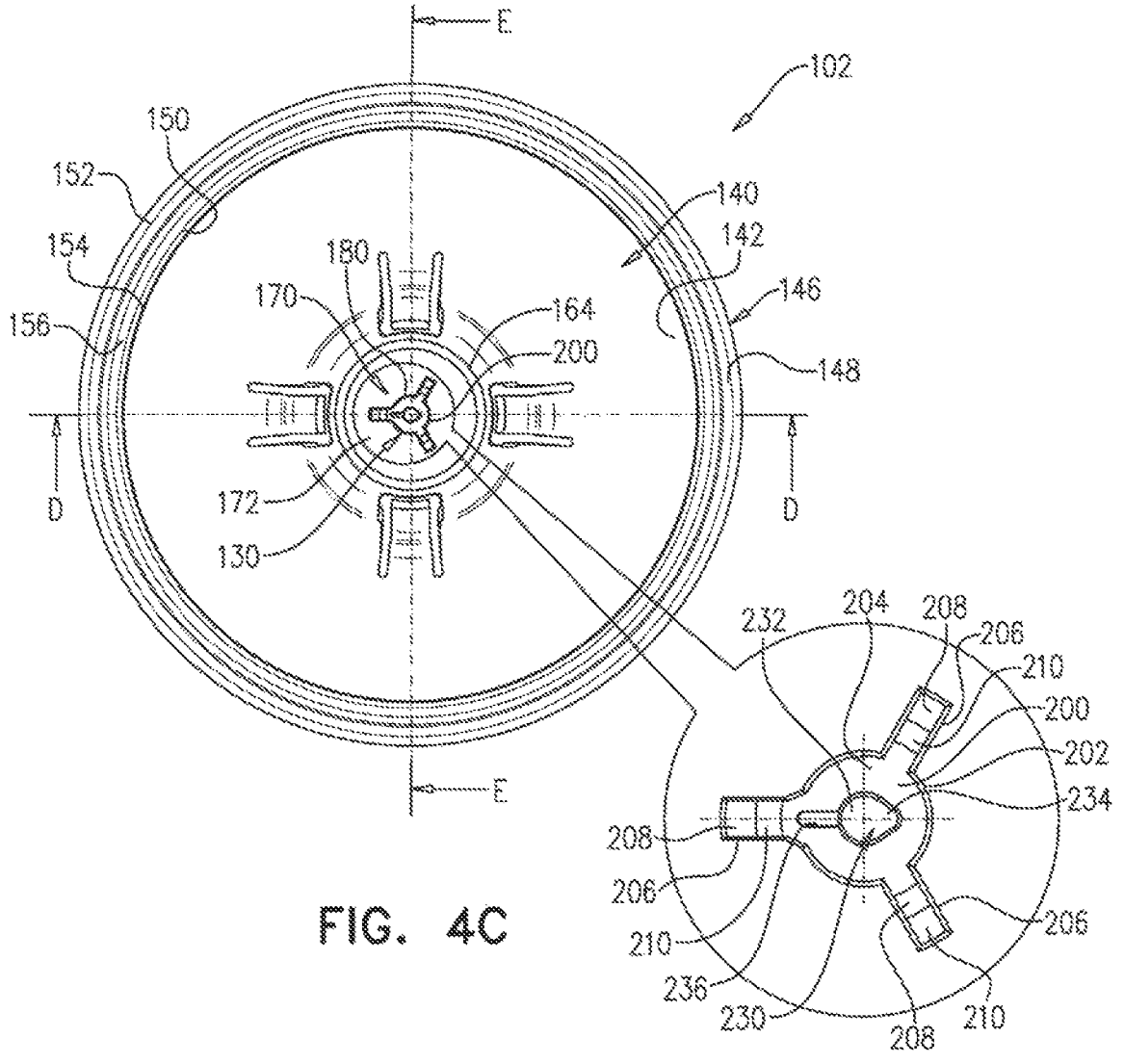
Figures 4D, 4E:
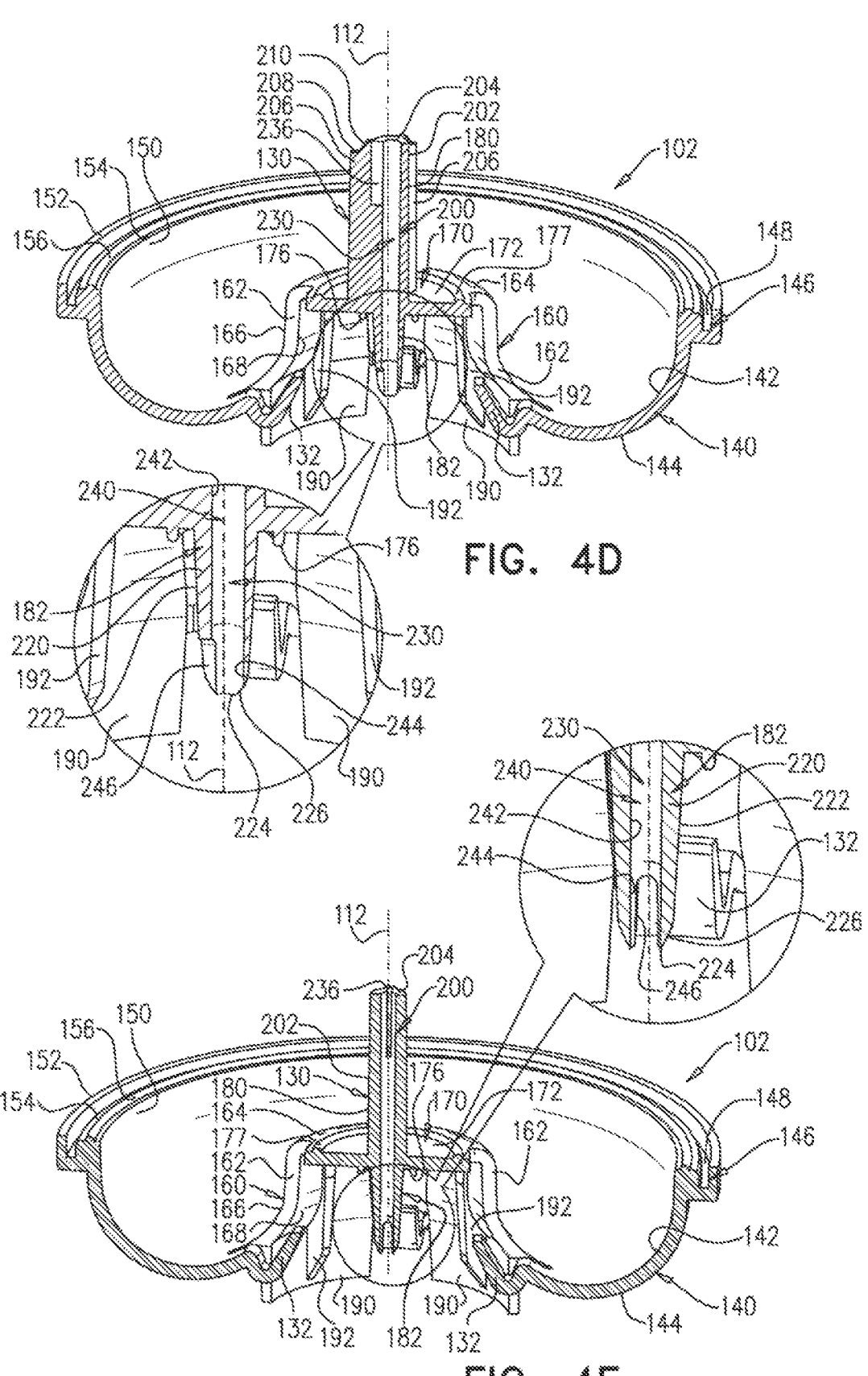
Figure 5A:
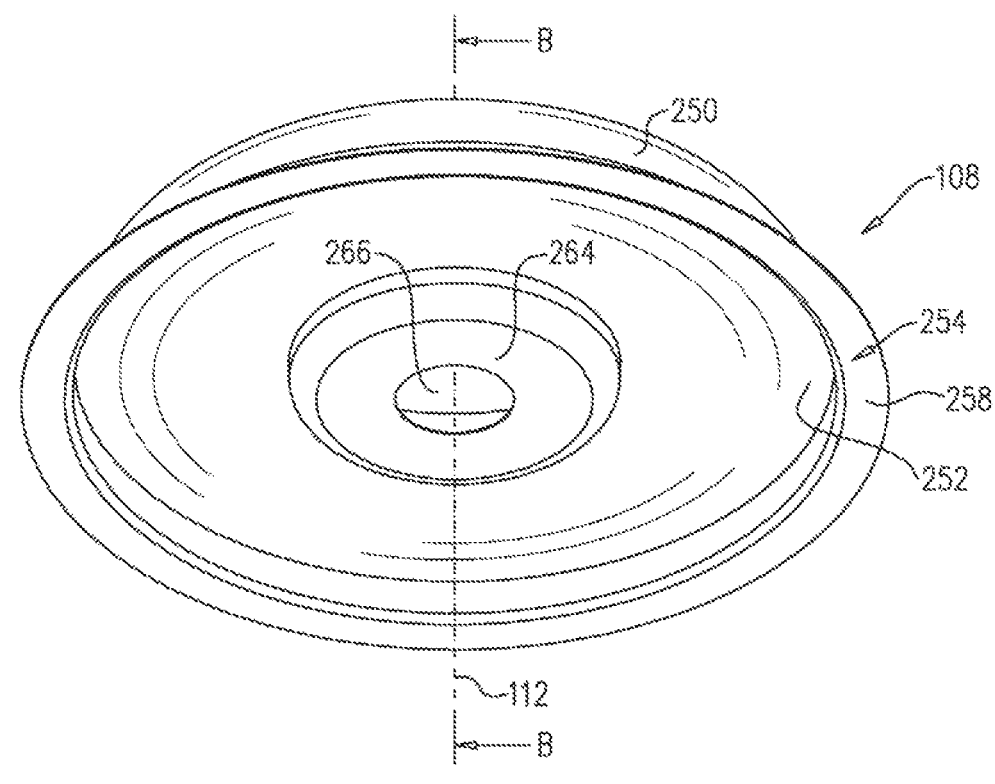
Figure 5B:
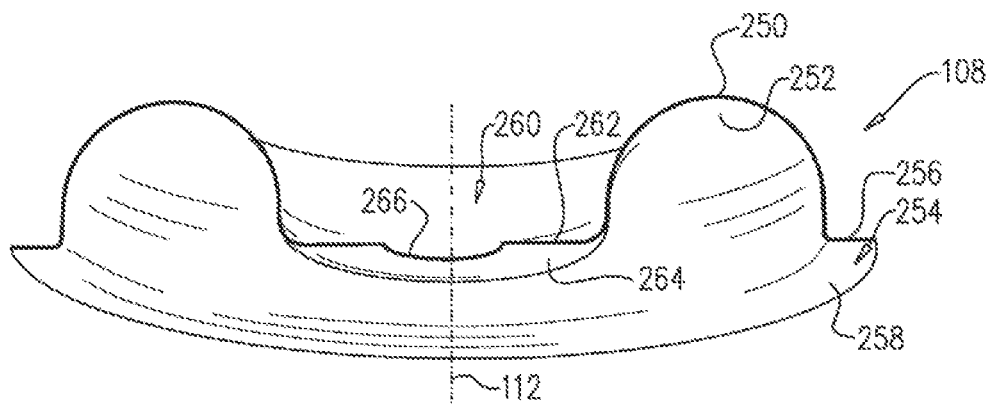
Figure 6B:
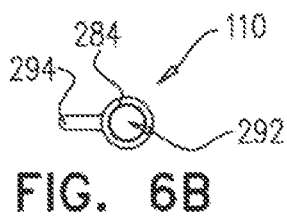
Figure 6A:
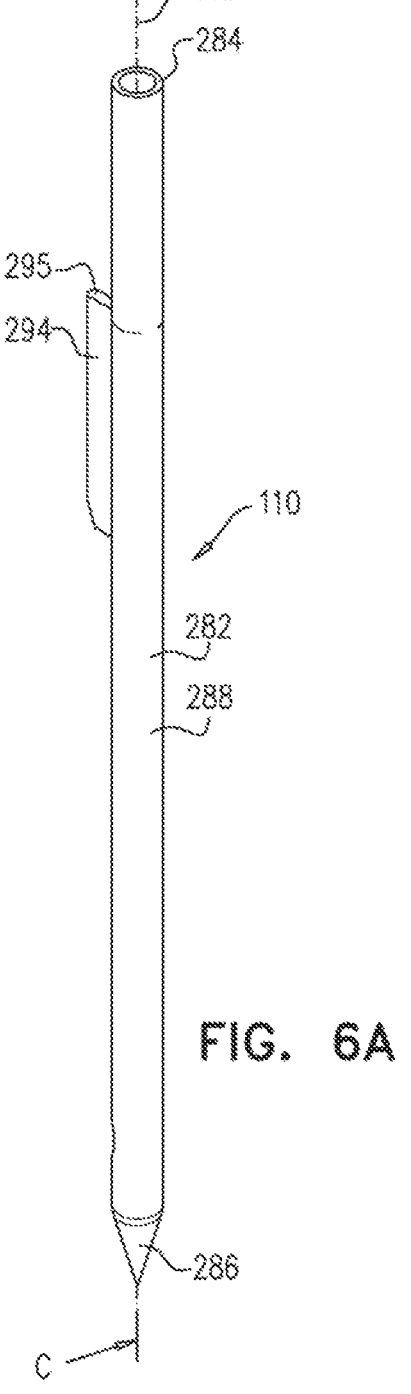
Figure 6C:
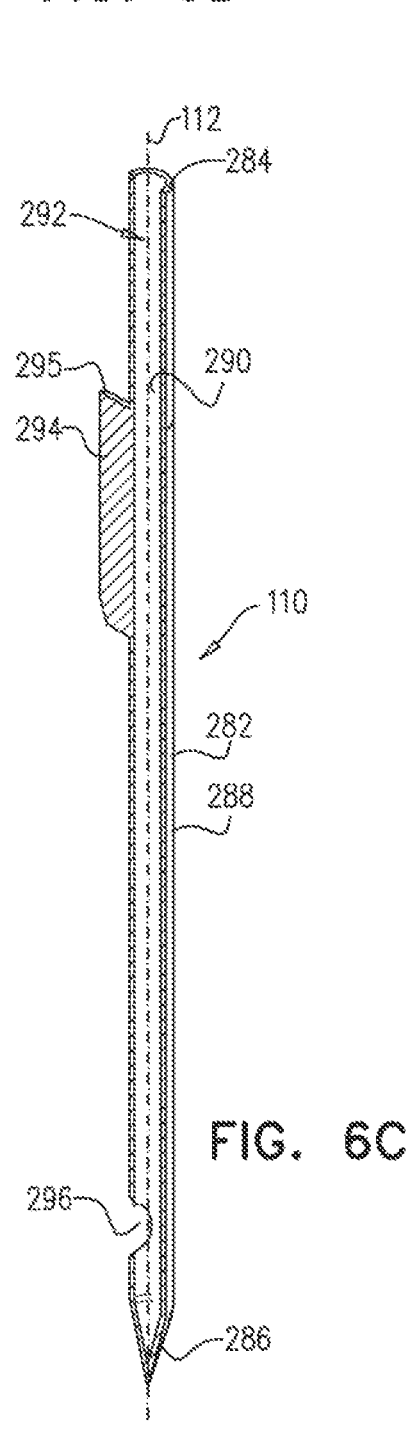
Figure 7A:
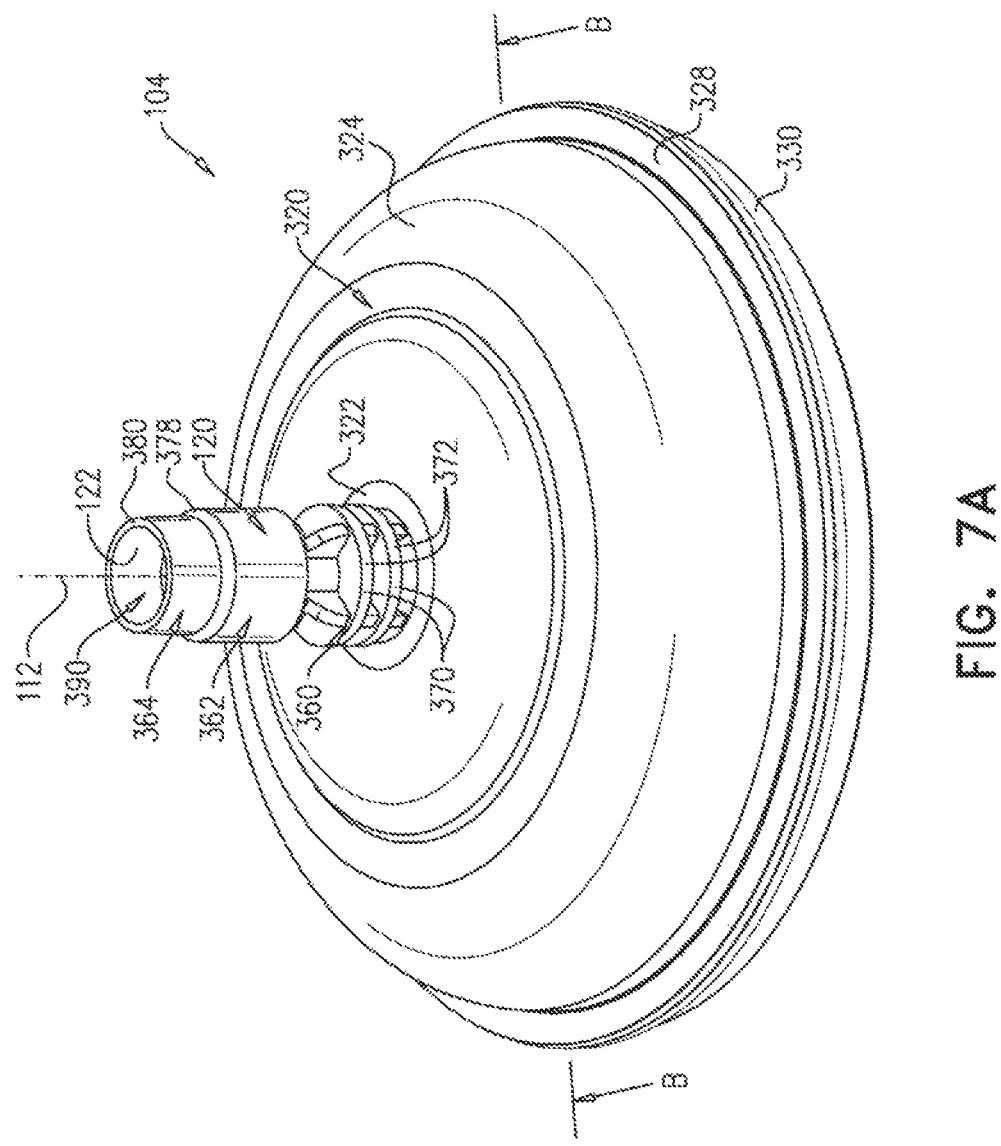
Figure 7B:
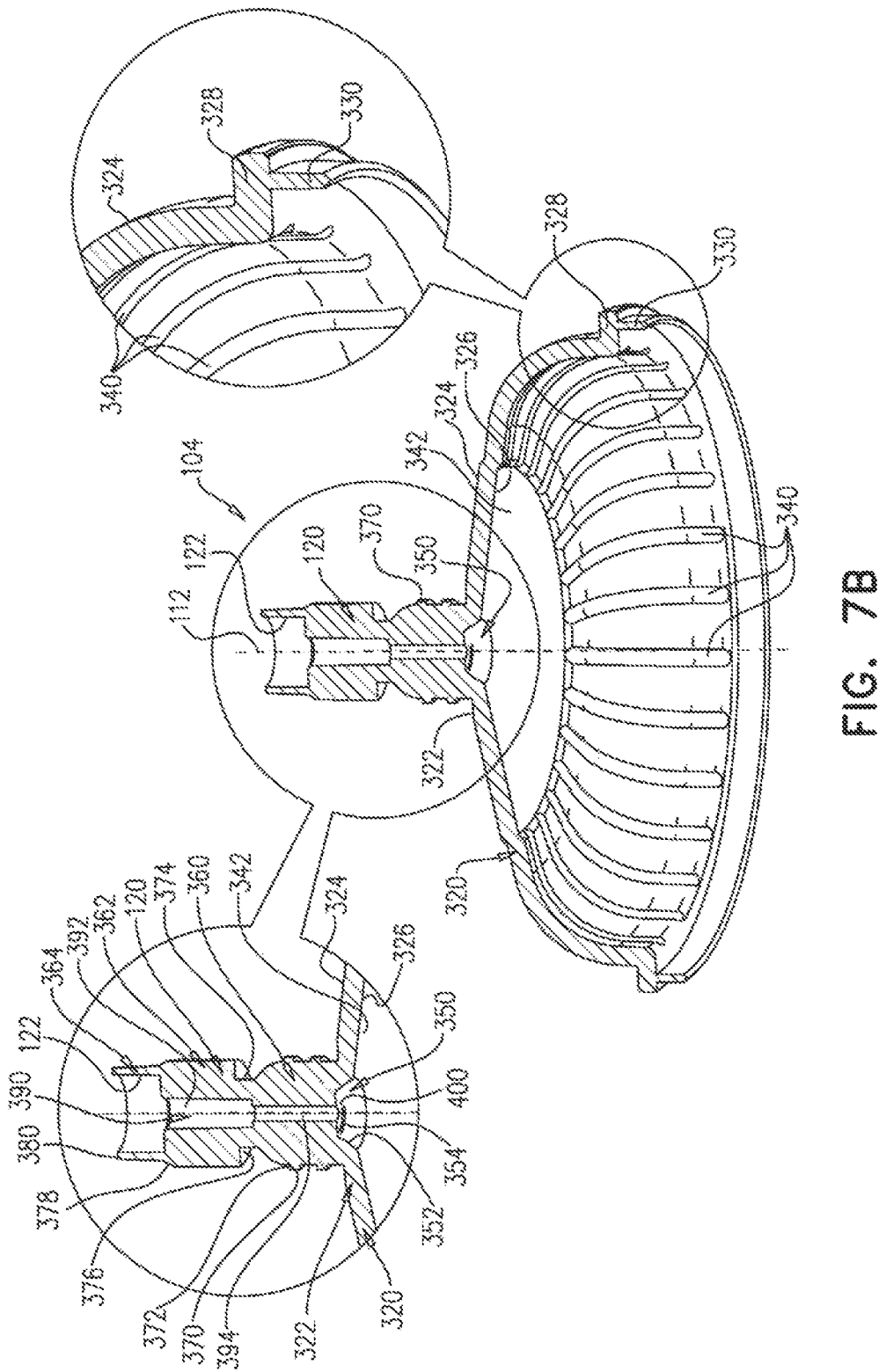
Figure 8A:
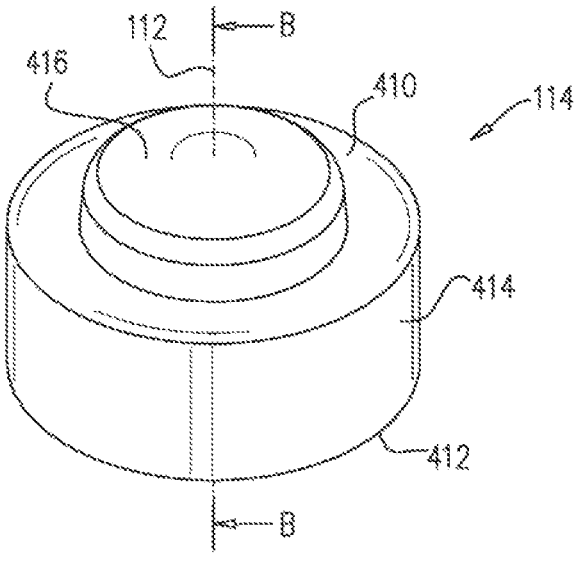
Figure 8B:
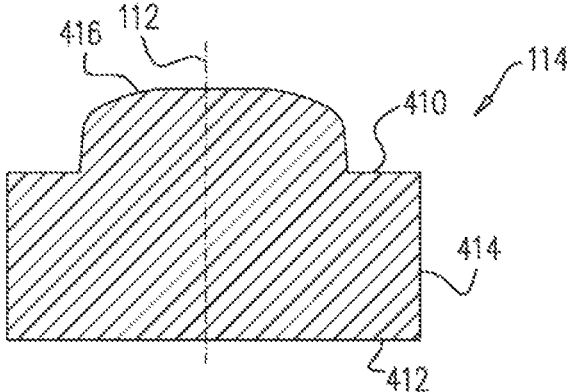
Figure 9A:
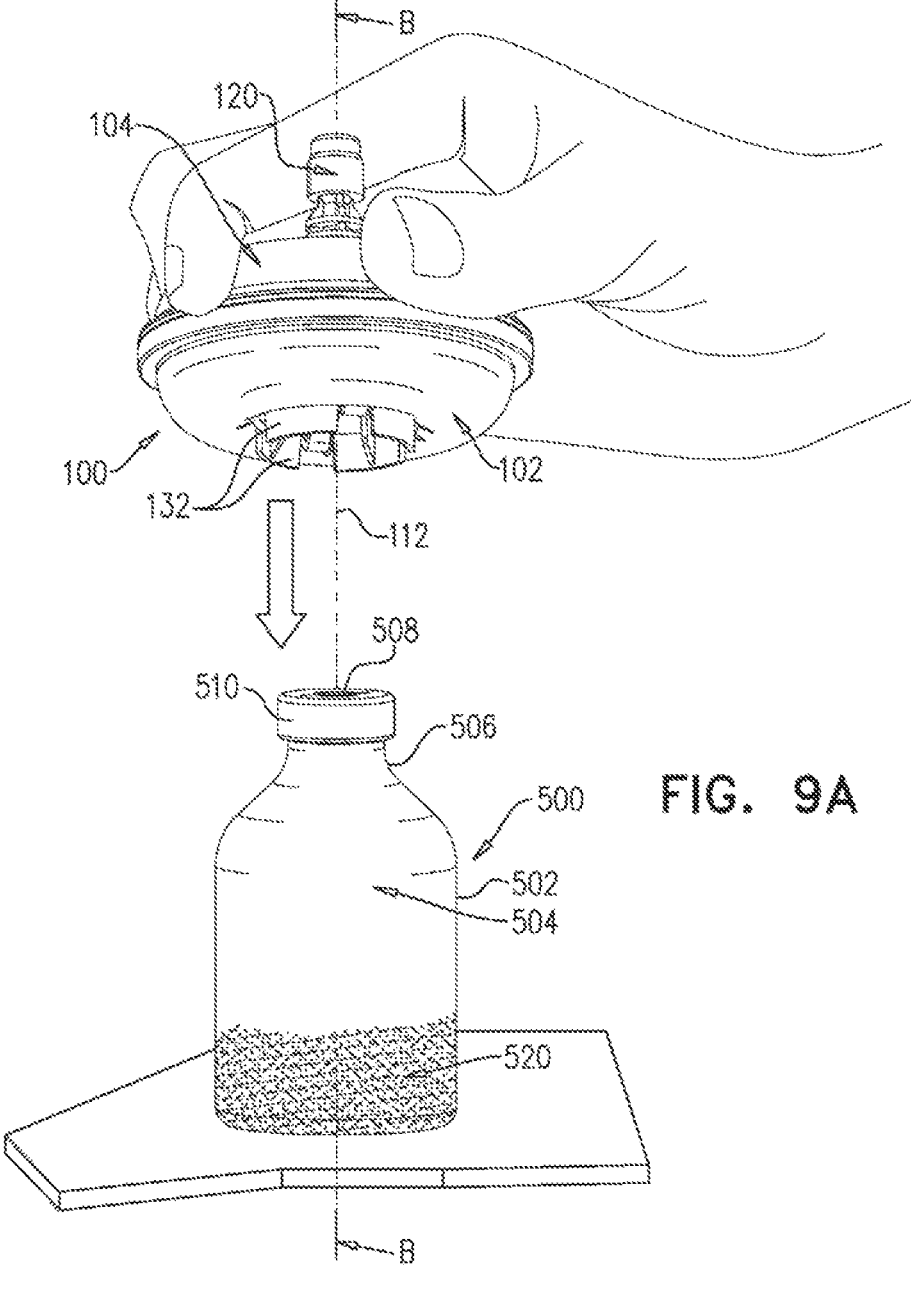
Figure 9B:
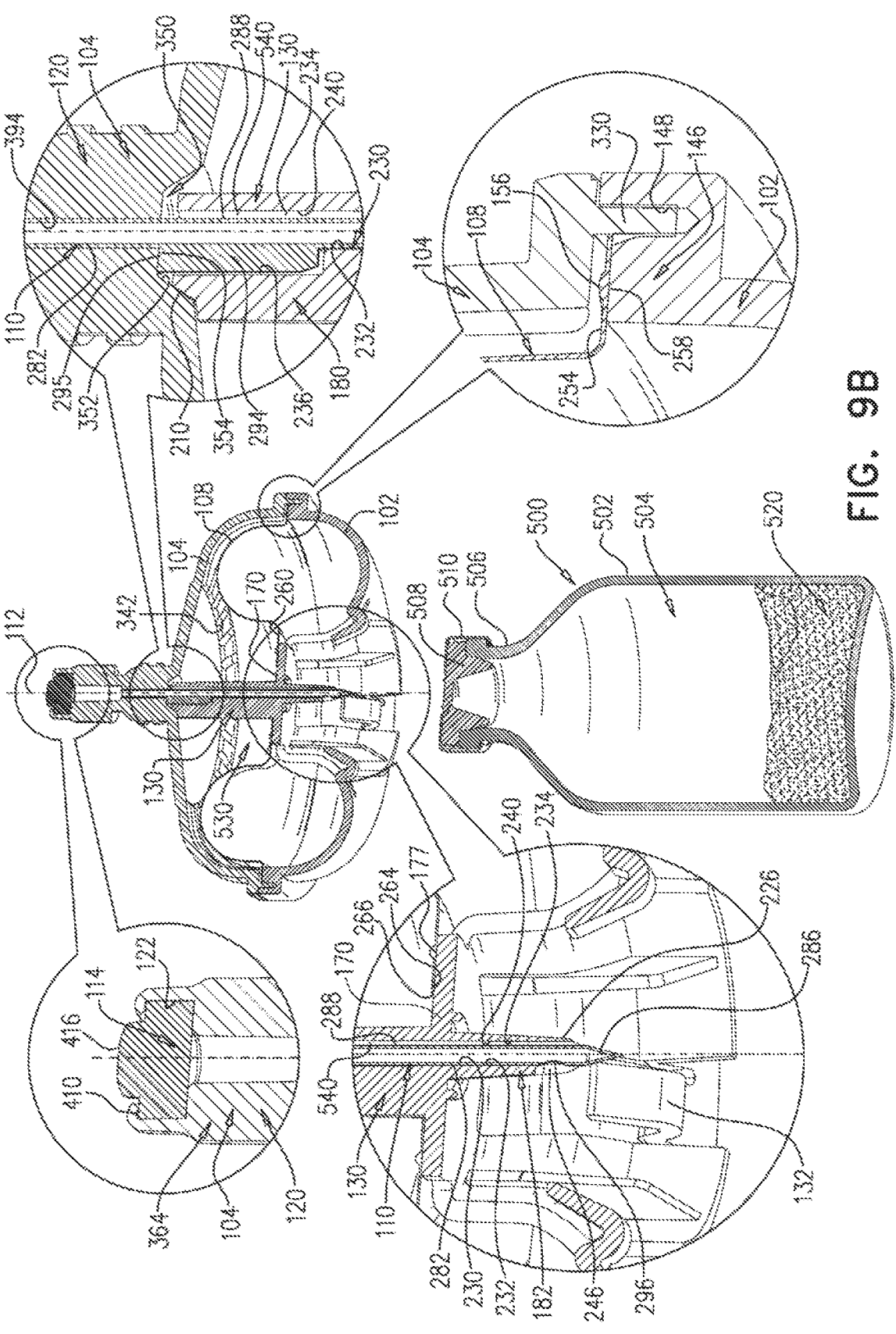
Figure 10A:
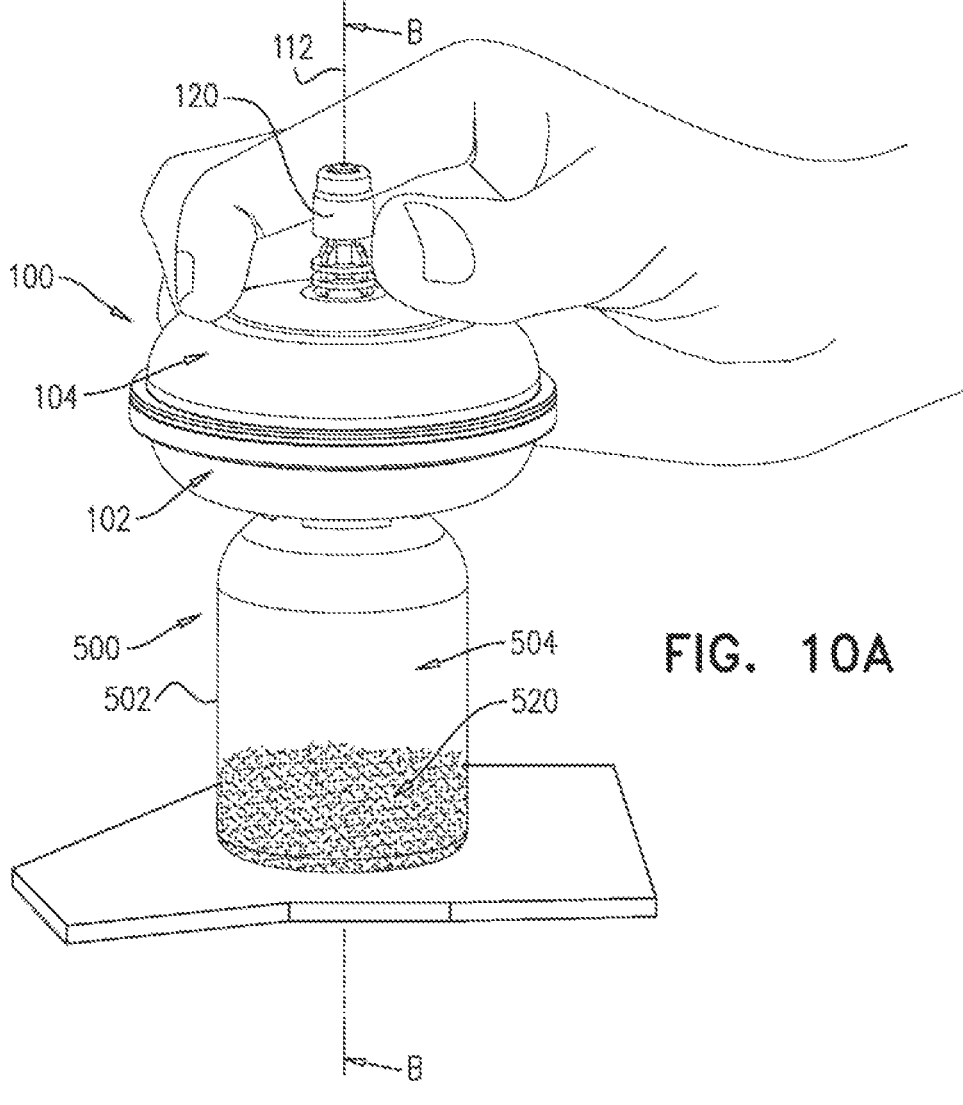
Figure 10B:
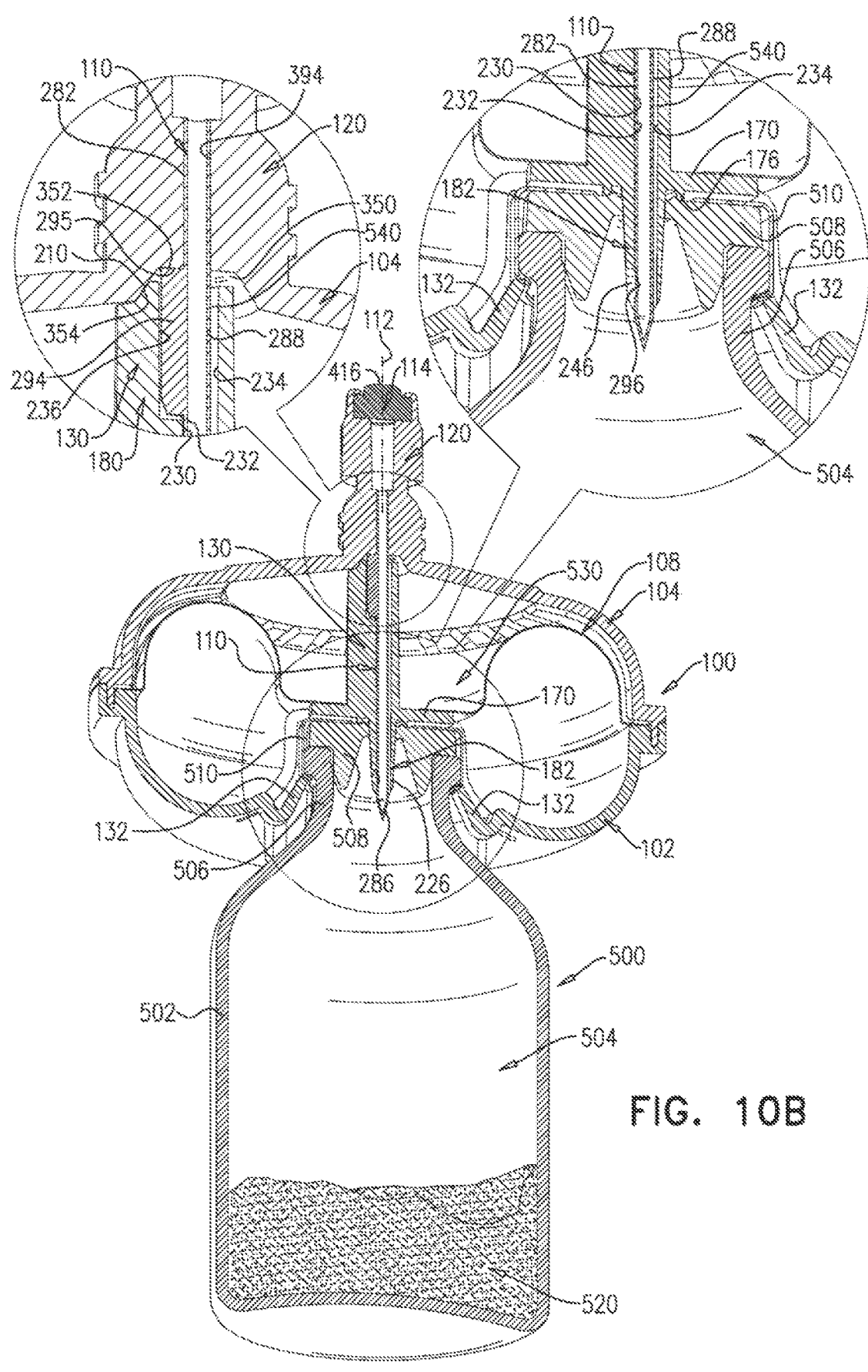
Figure 11A:
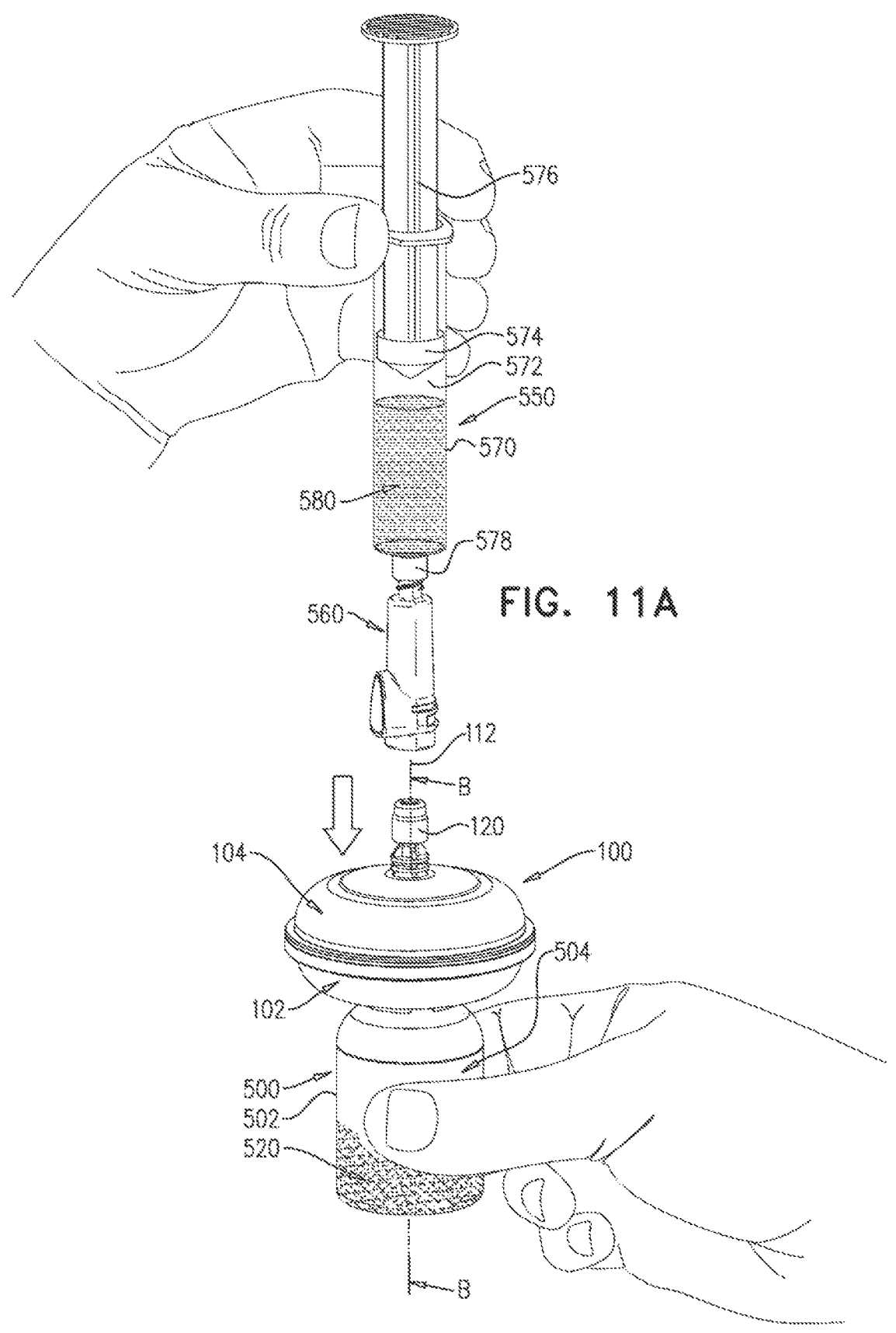
Figure 11B:
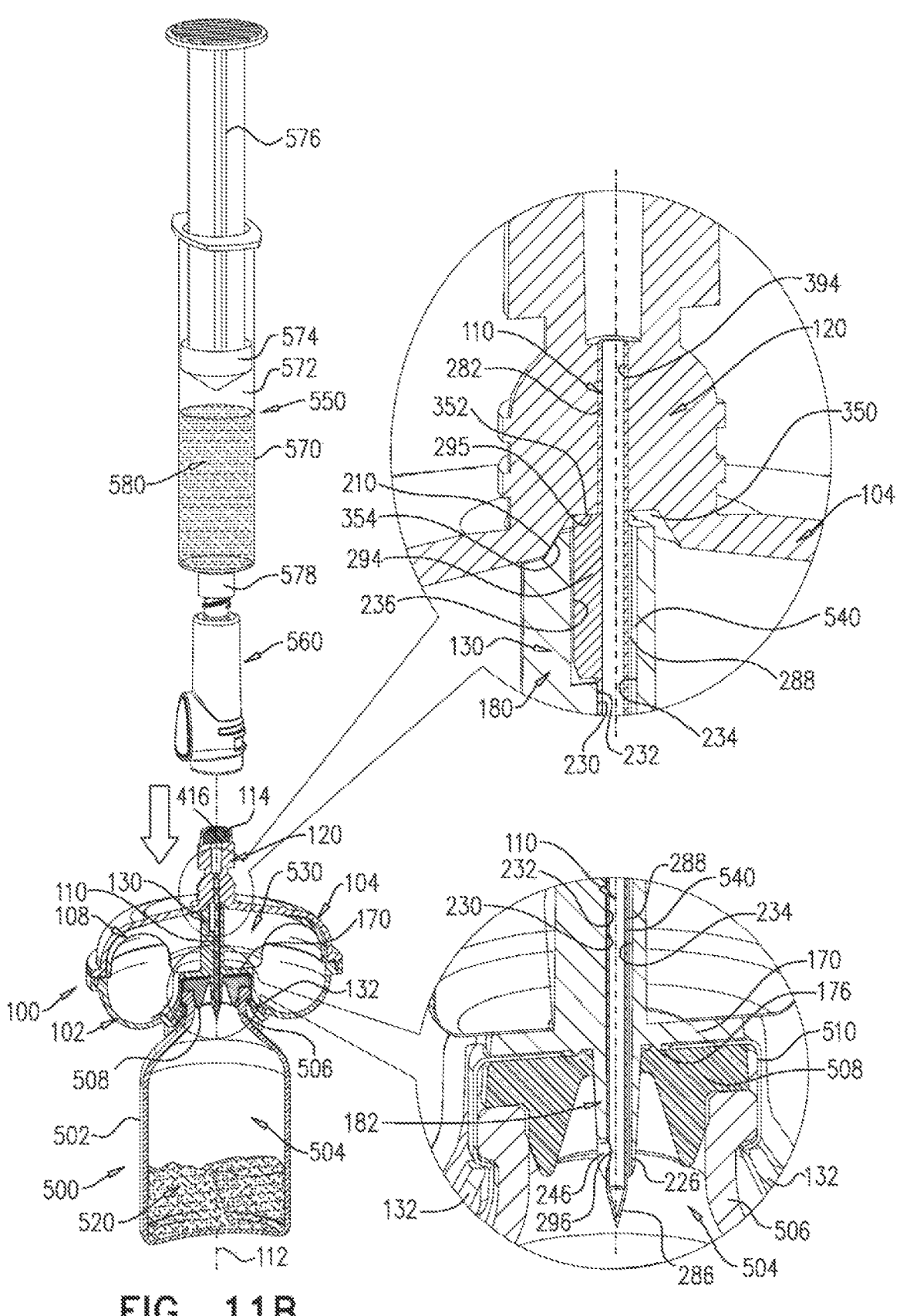
Figure 12A:
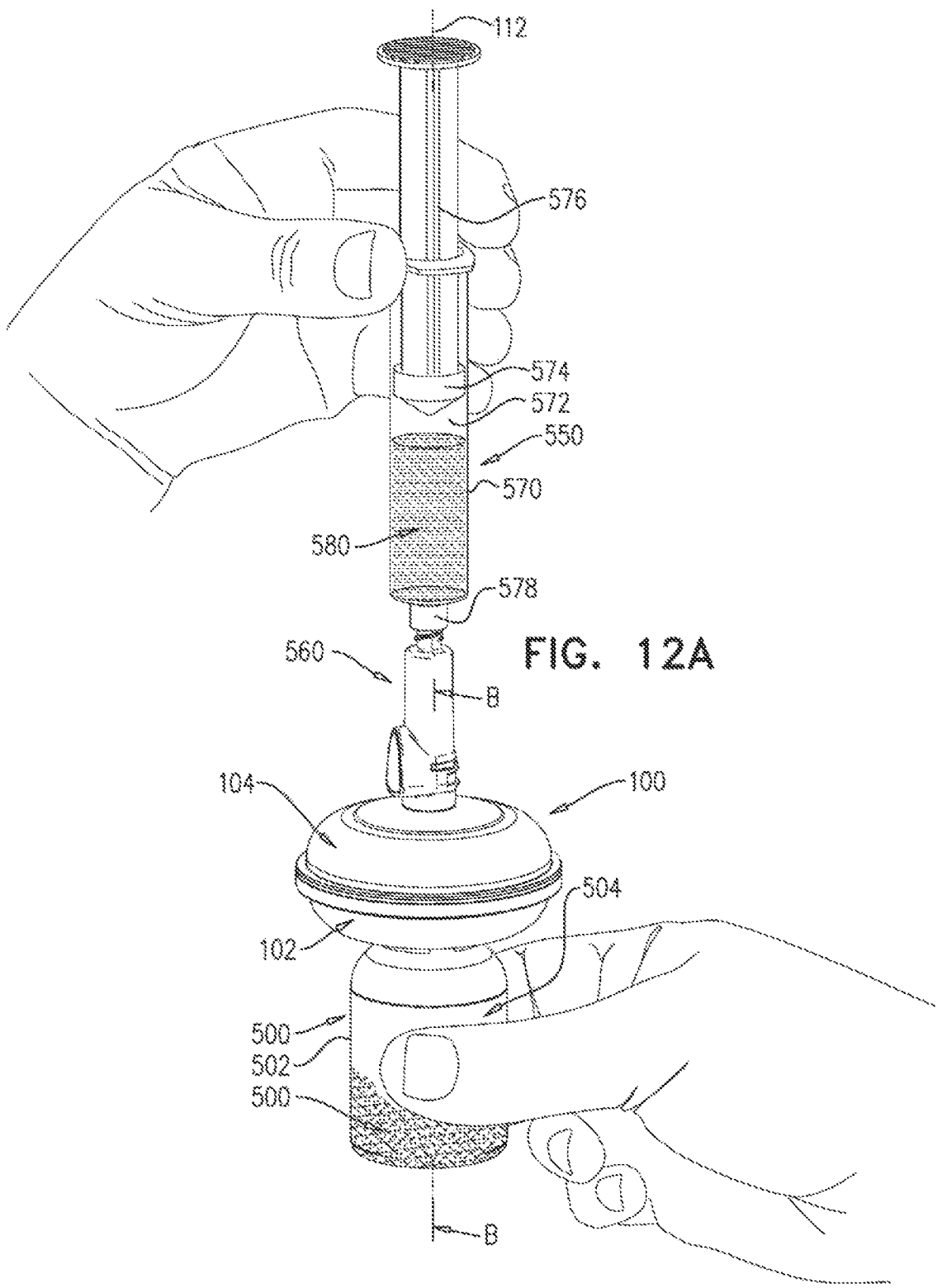
Figure 12B:
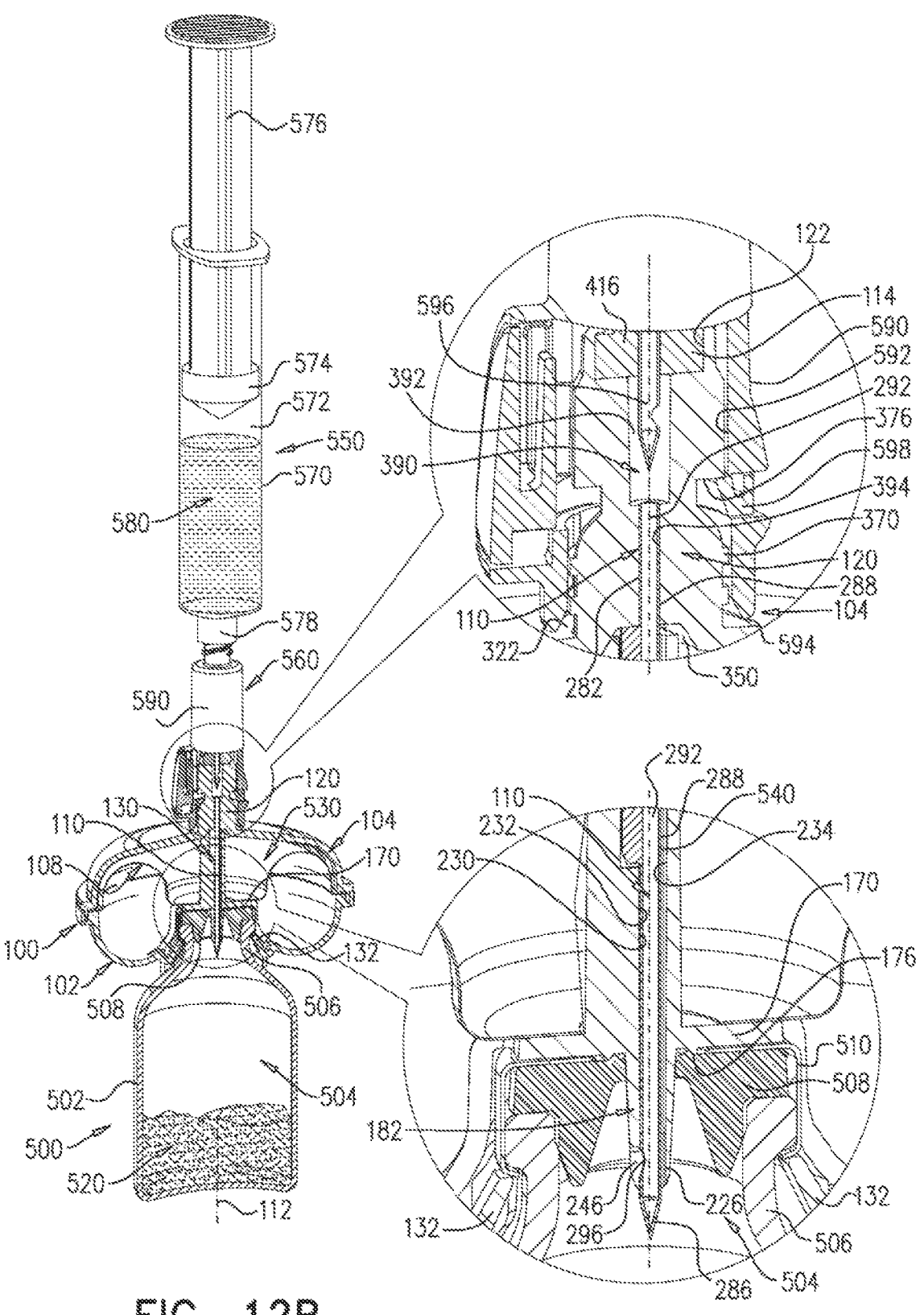
Figure 13A:
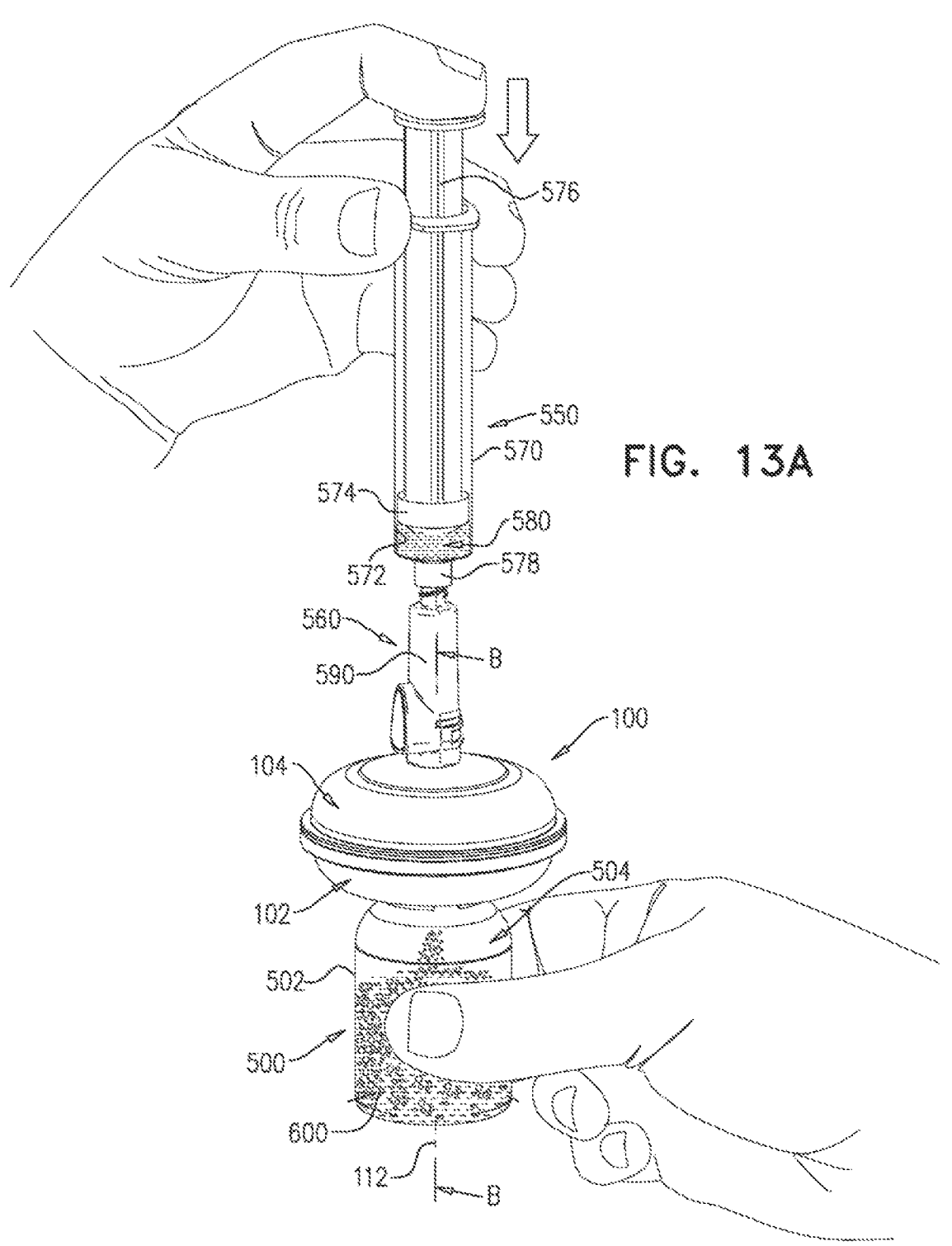
Figure 13B:
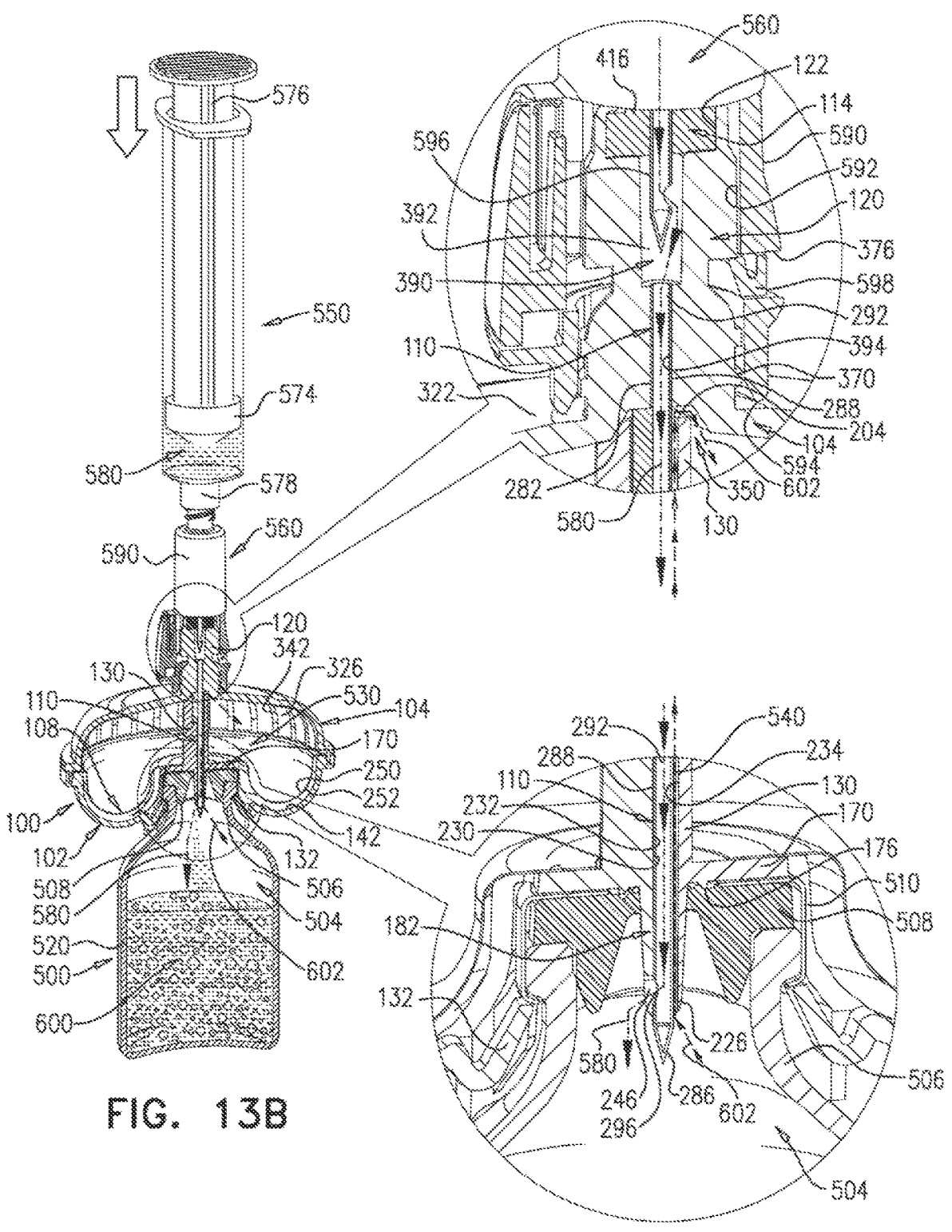
Figure 14A:
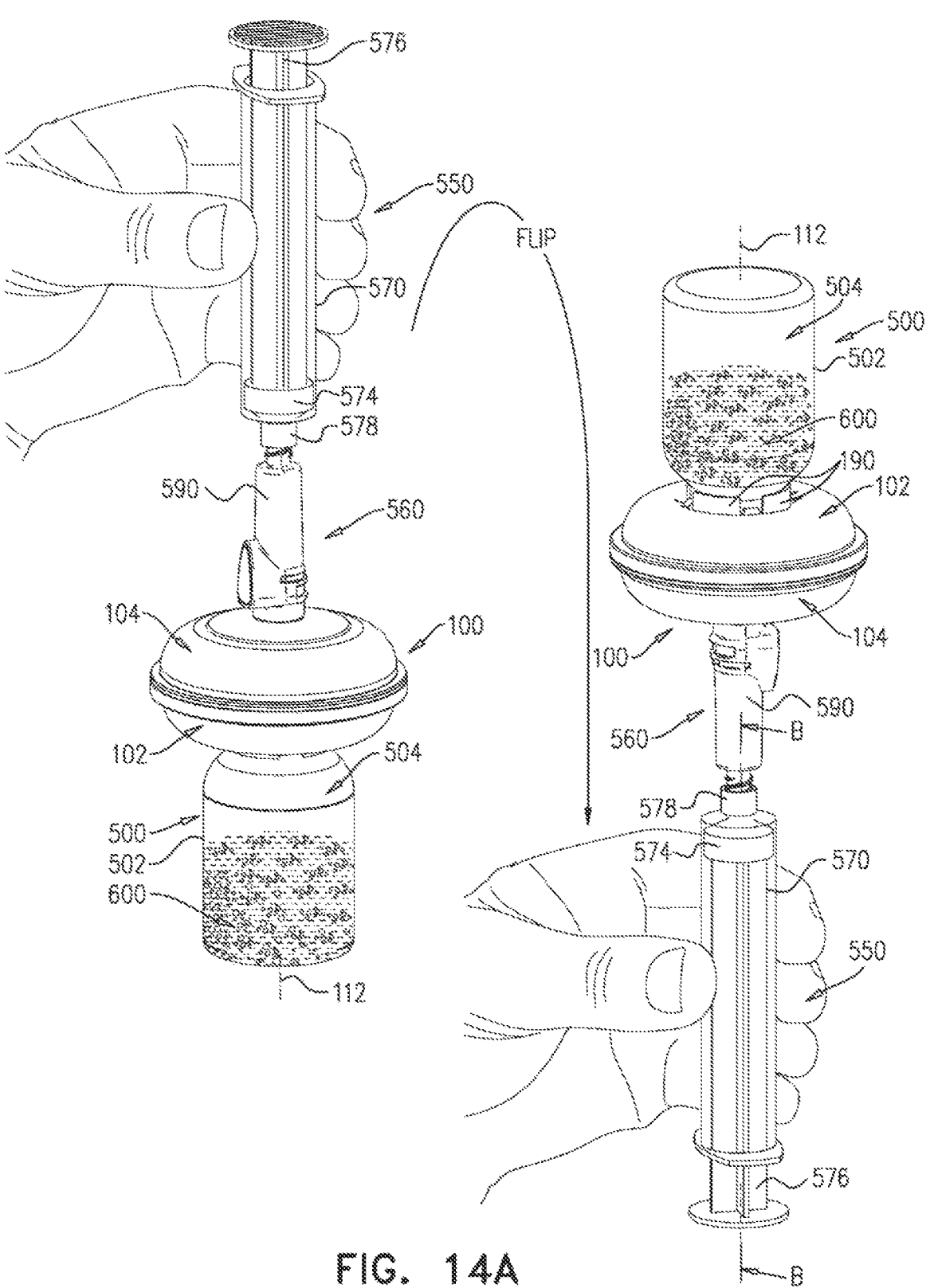
Figure 14B:
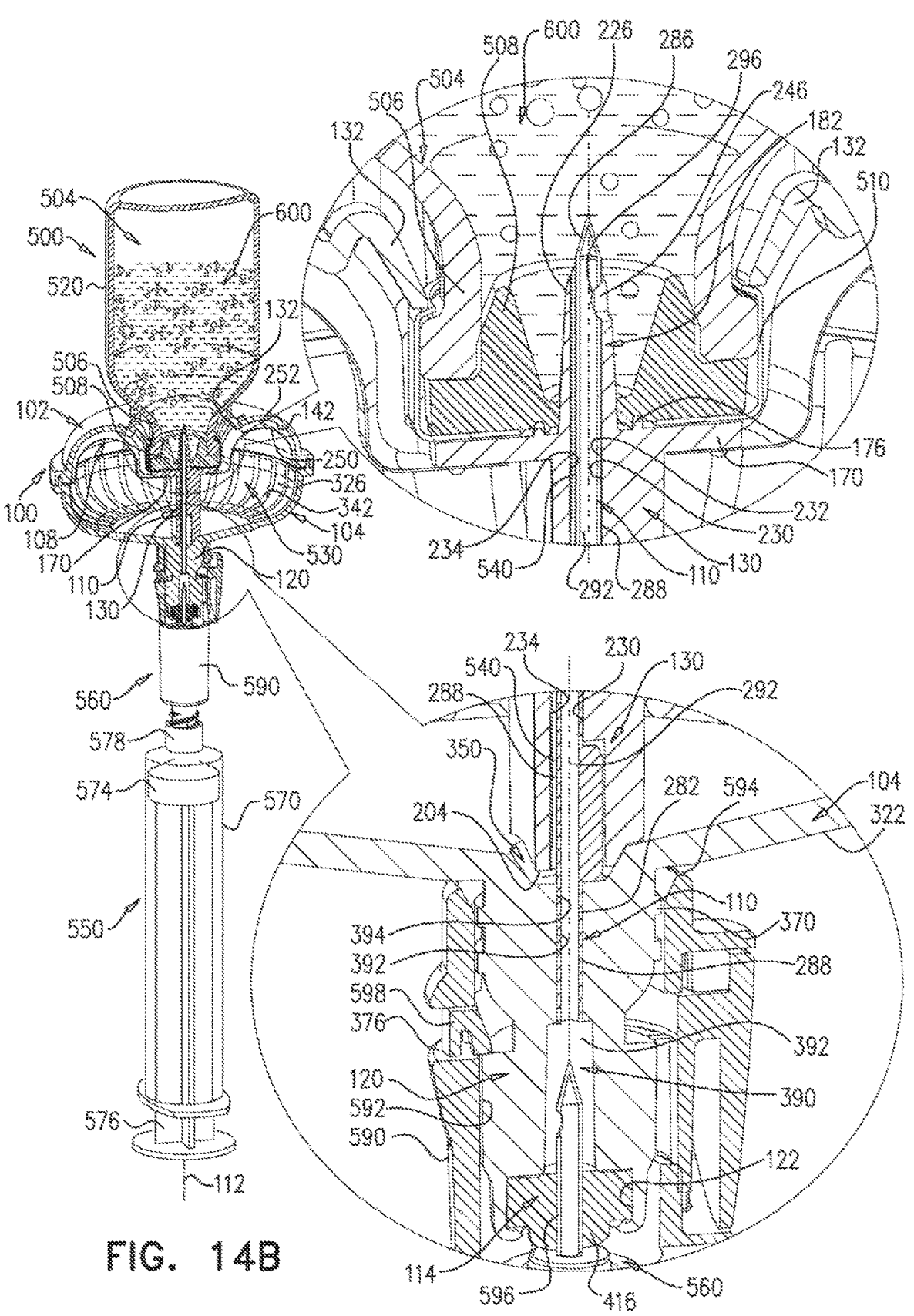
Figure 15A:
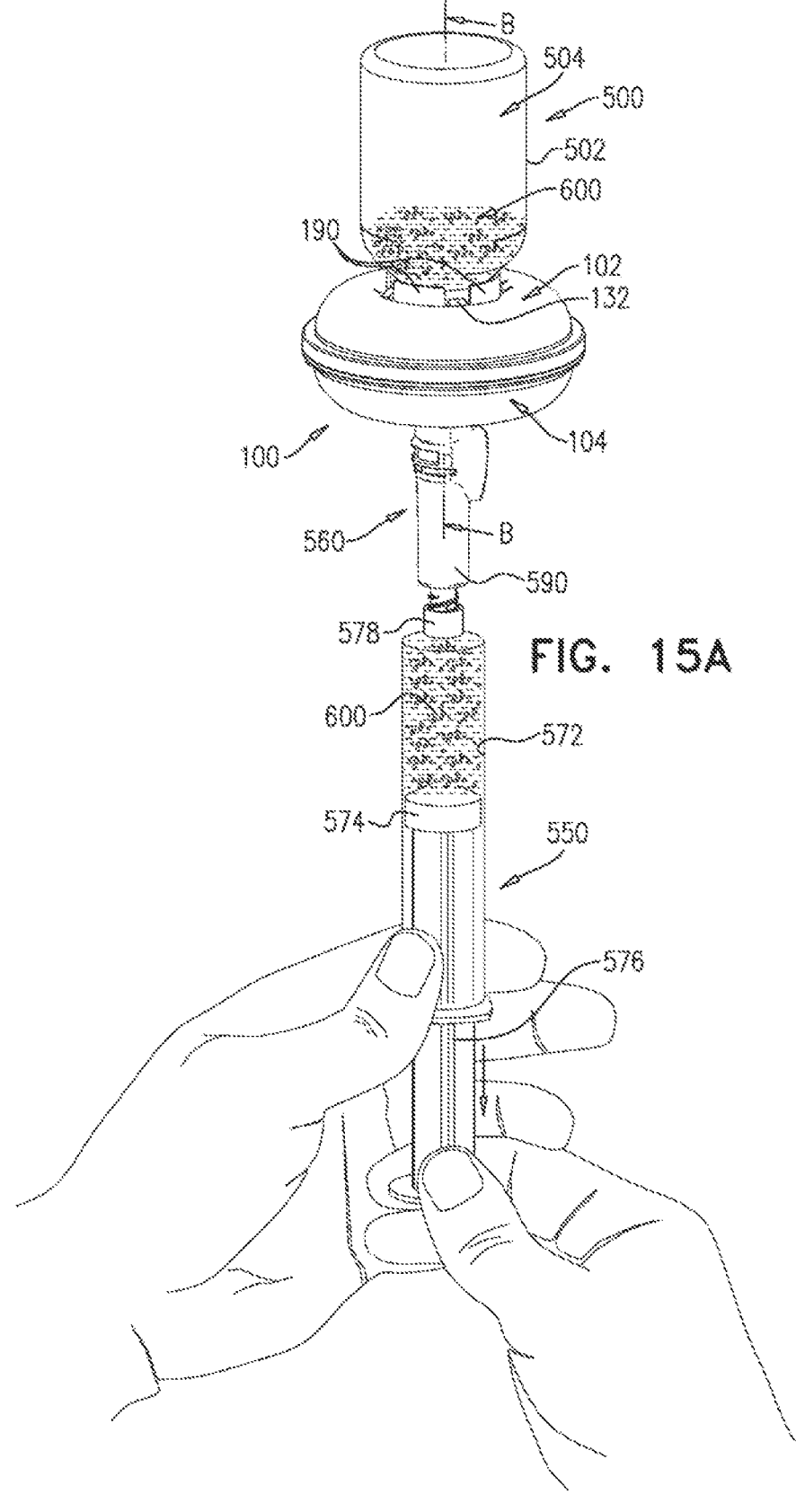
Figure 15B:
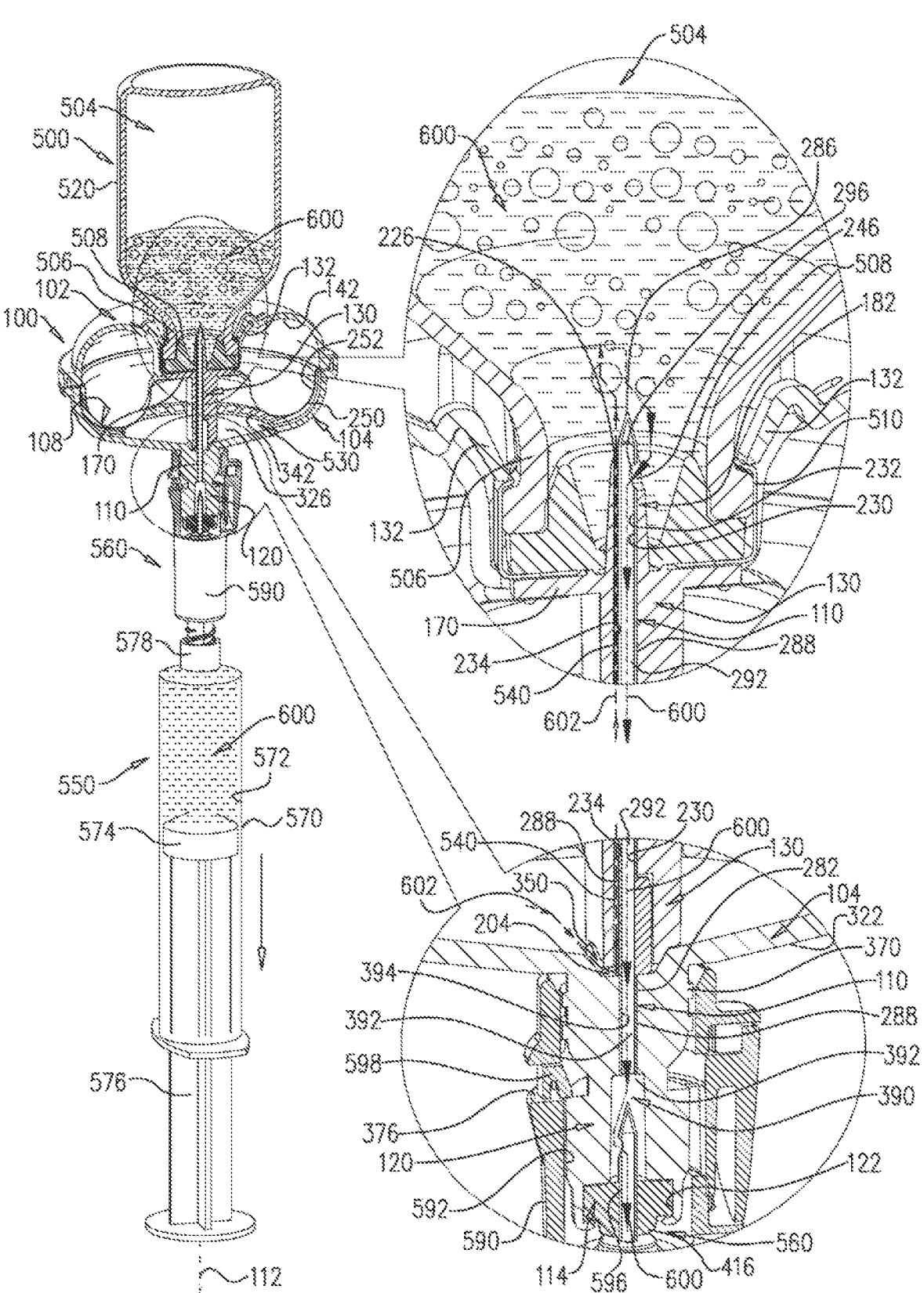
Figure 16A:
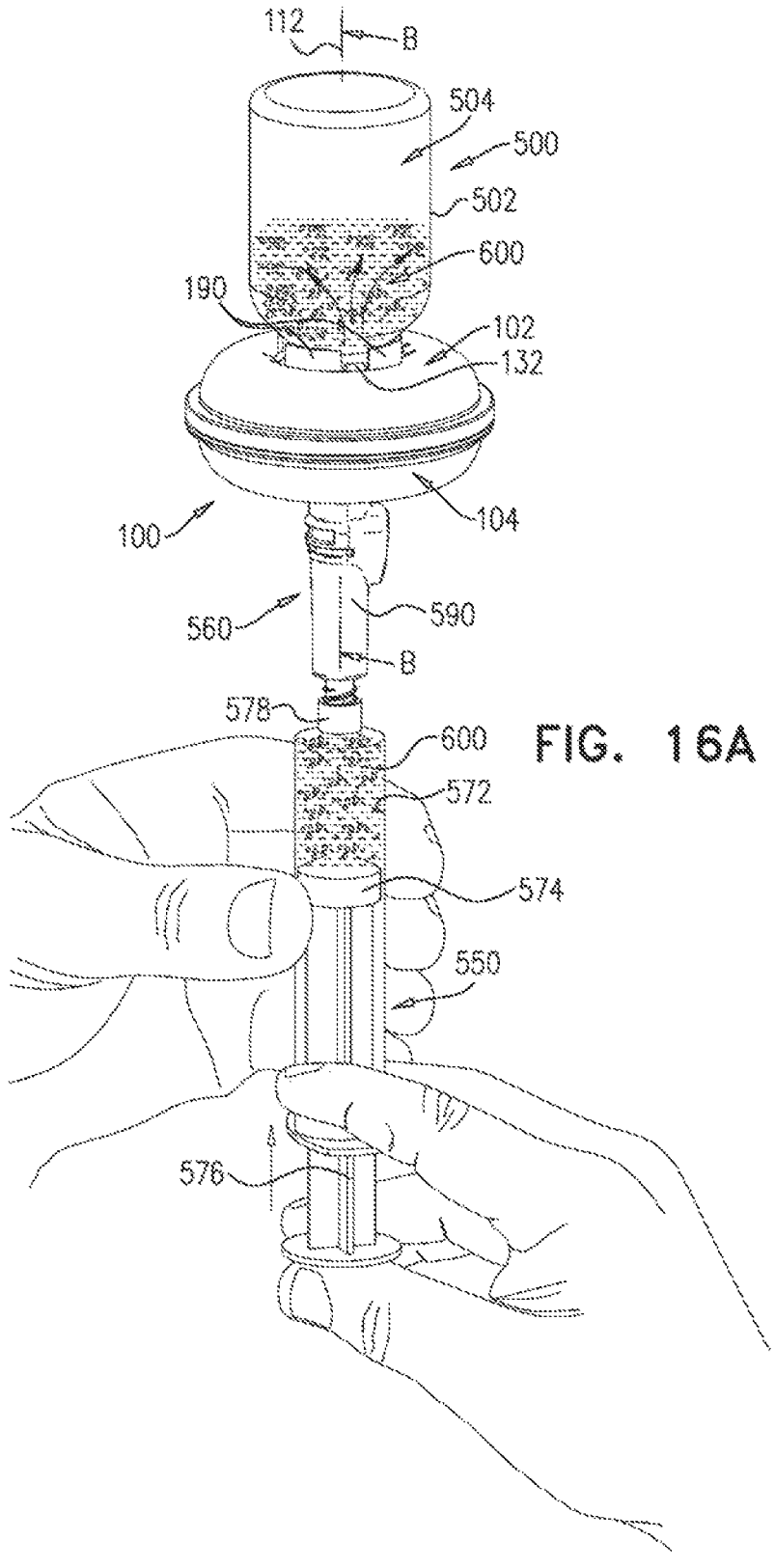
Figure 16B:
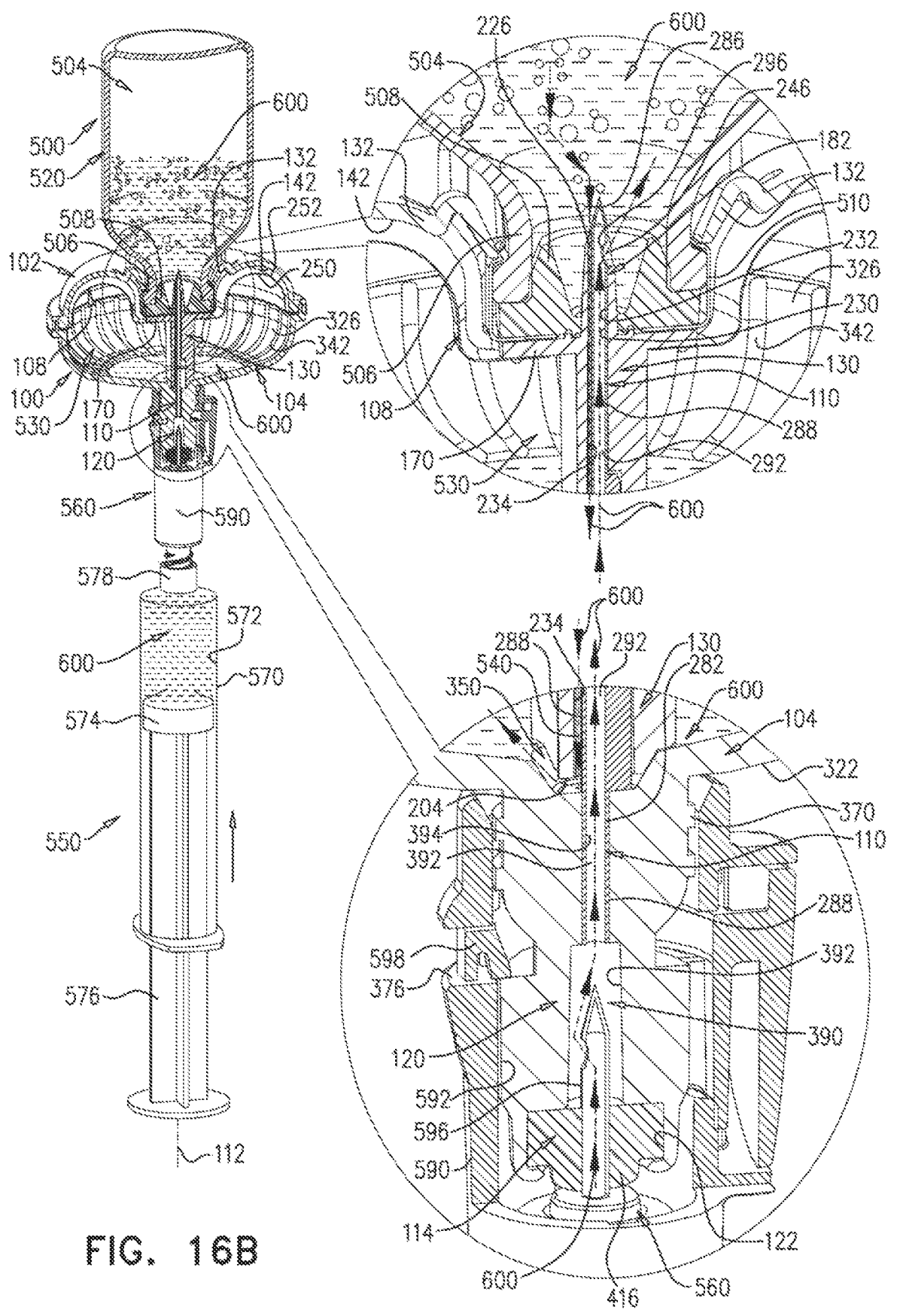
Figure 17A:
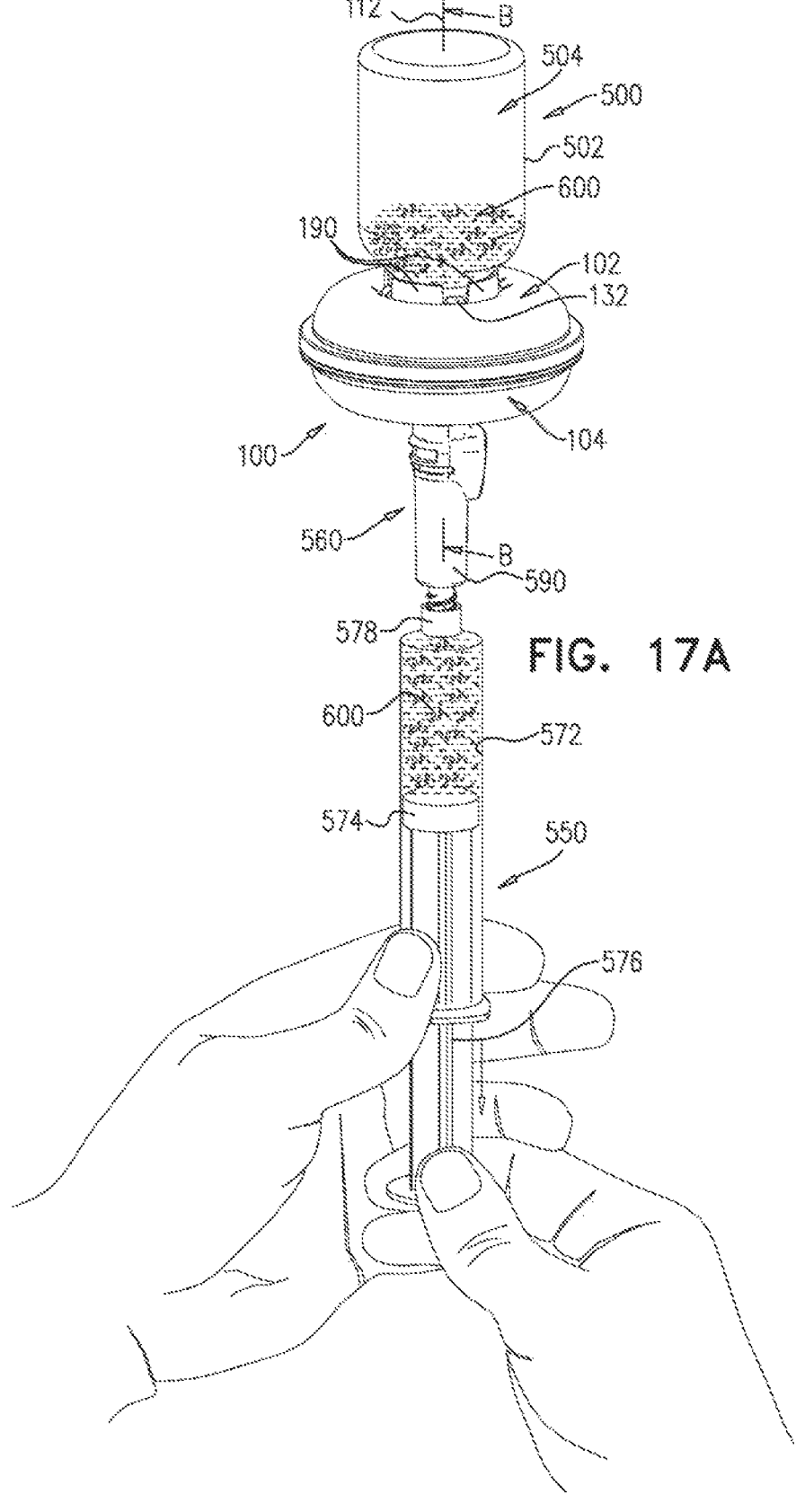
Figure 17B:
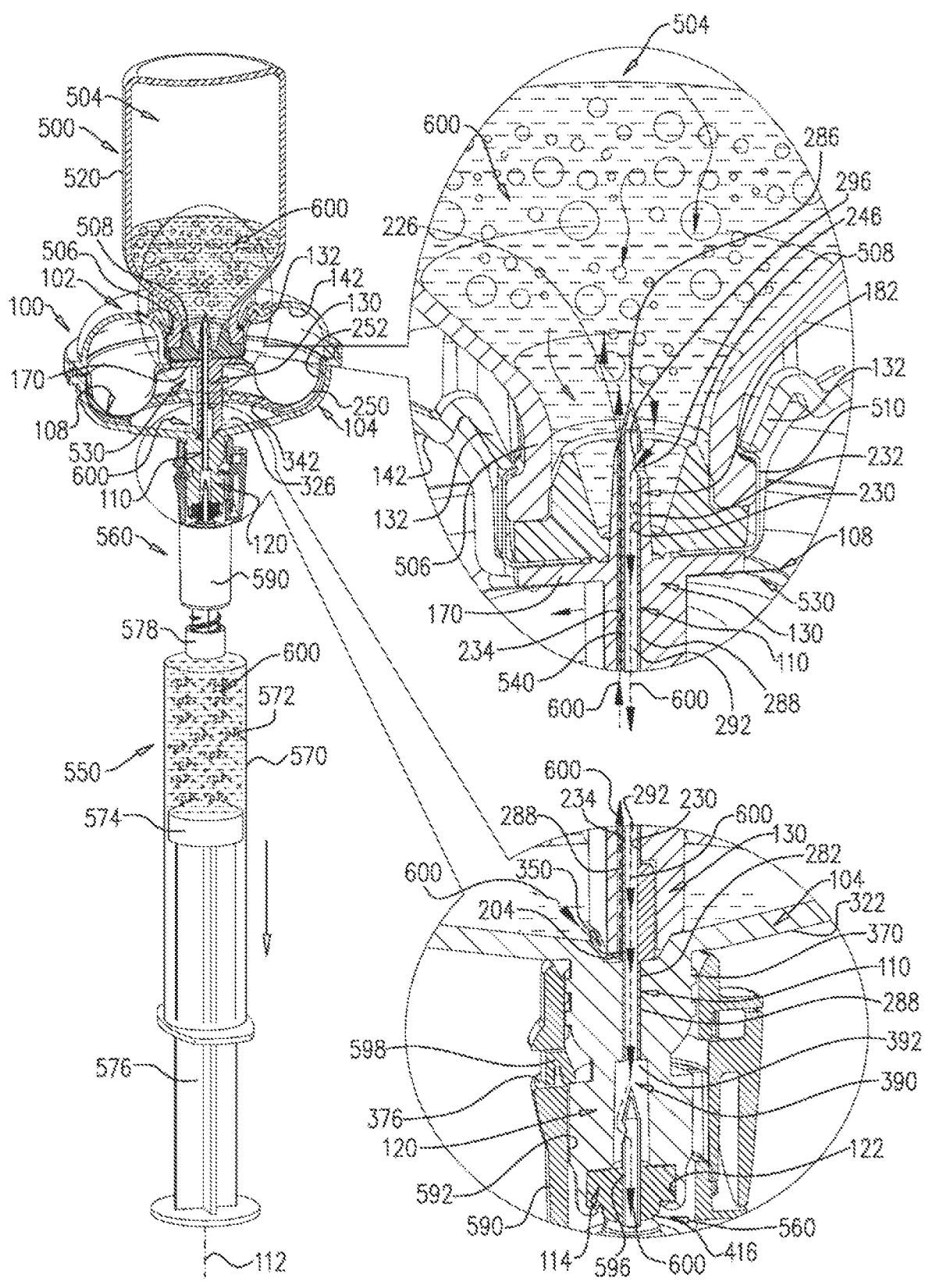
Figure 18A:
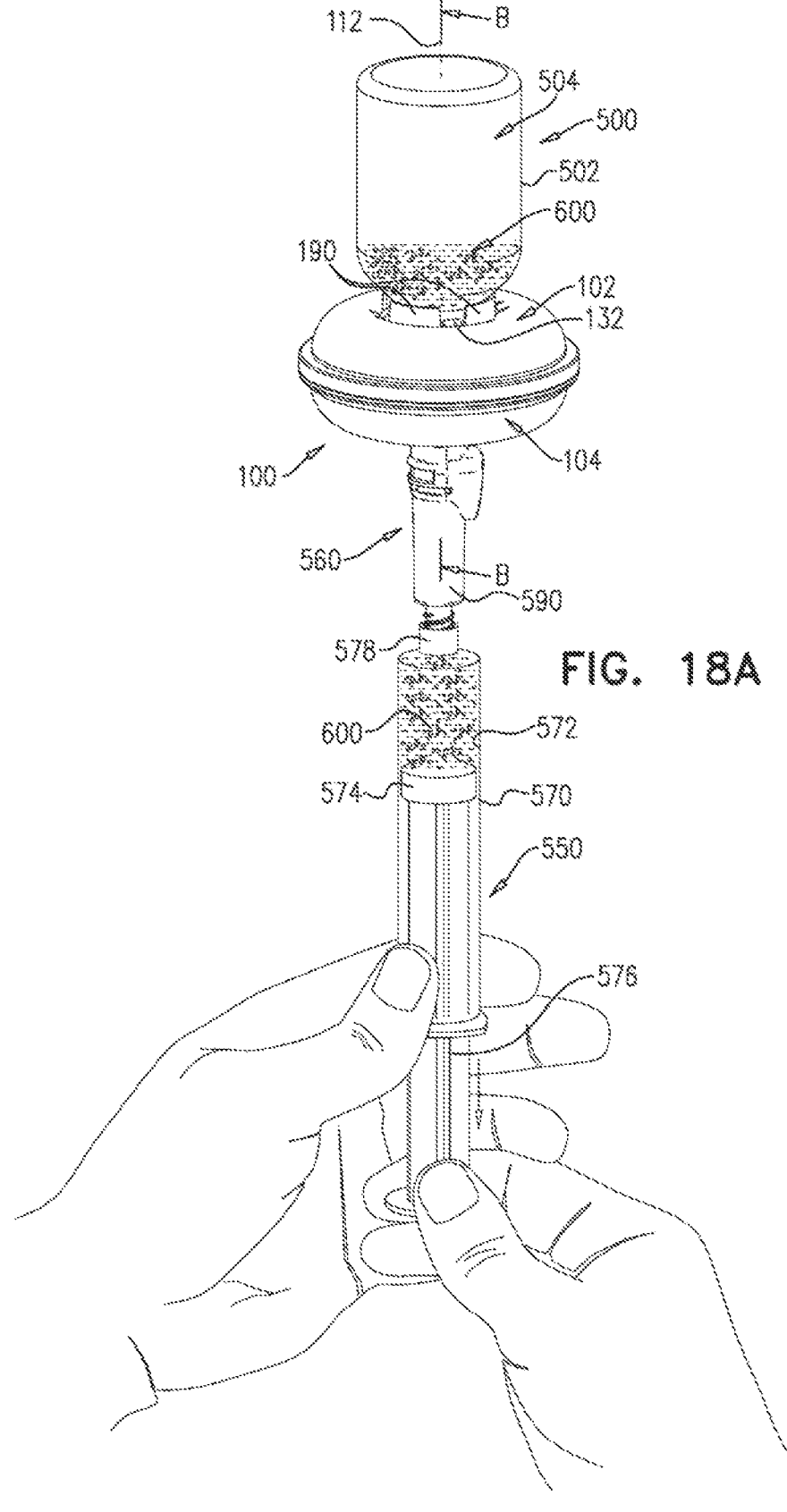
Figure 18B:
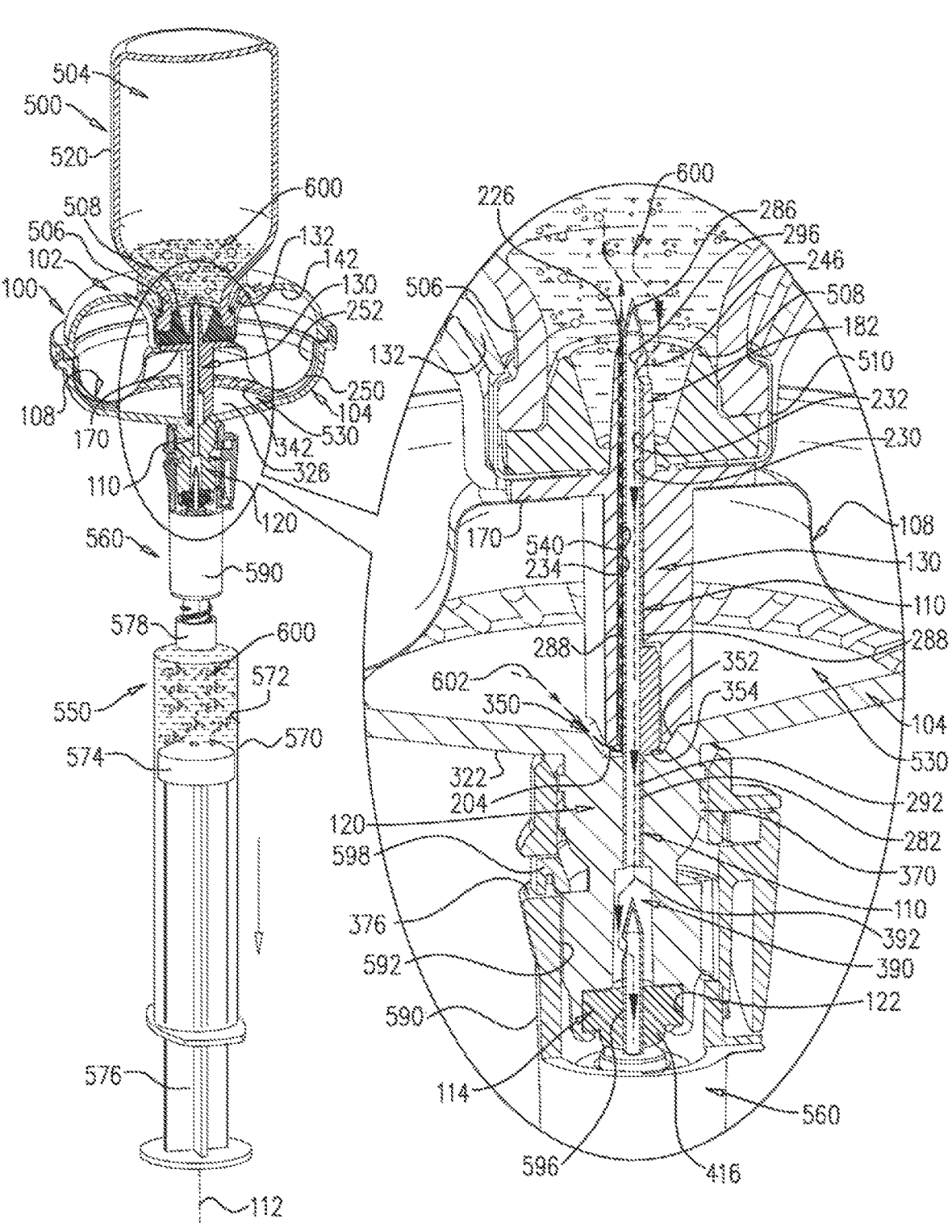
Figure 19A:
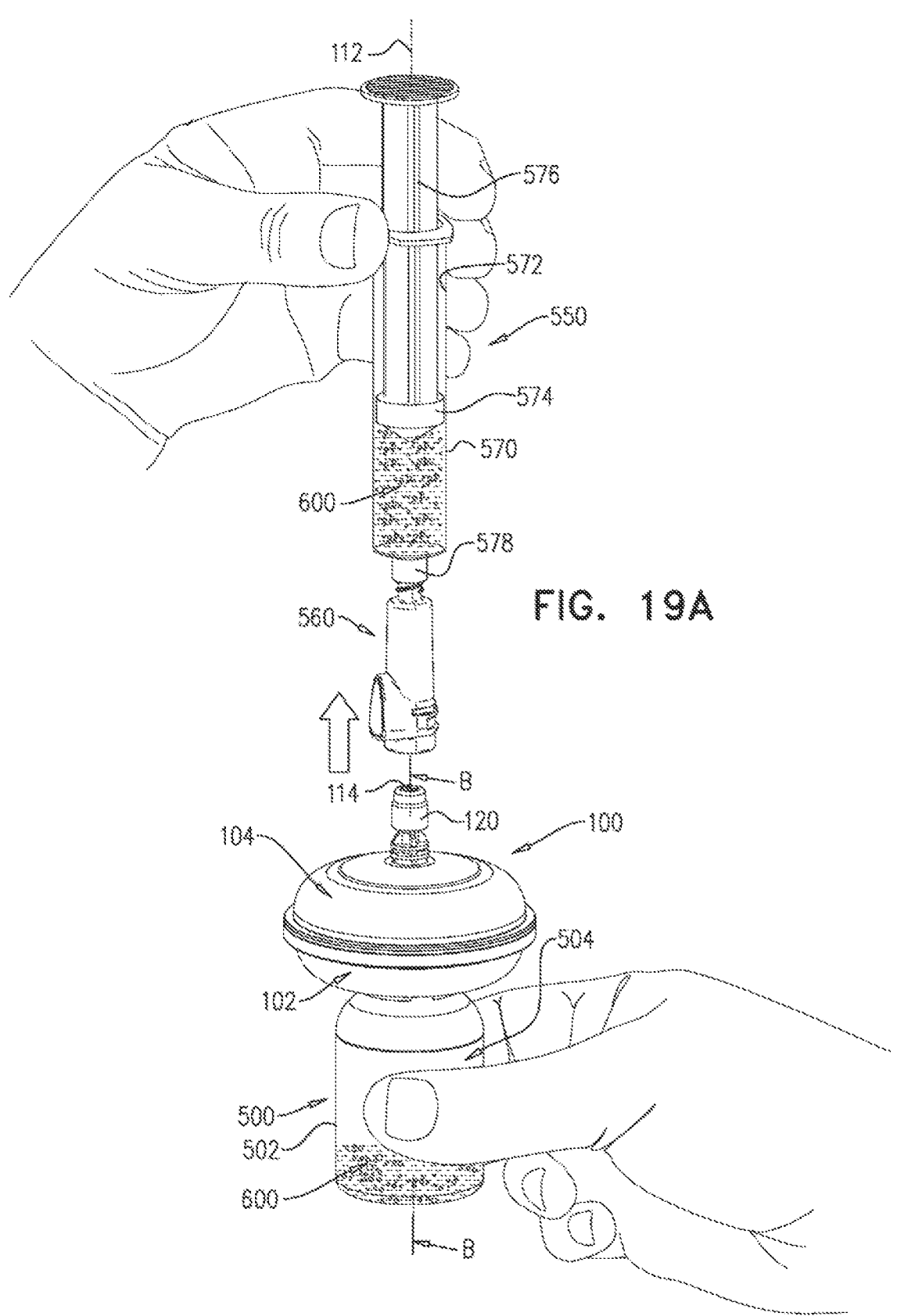
Figure 19B:
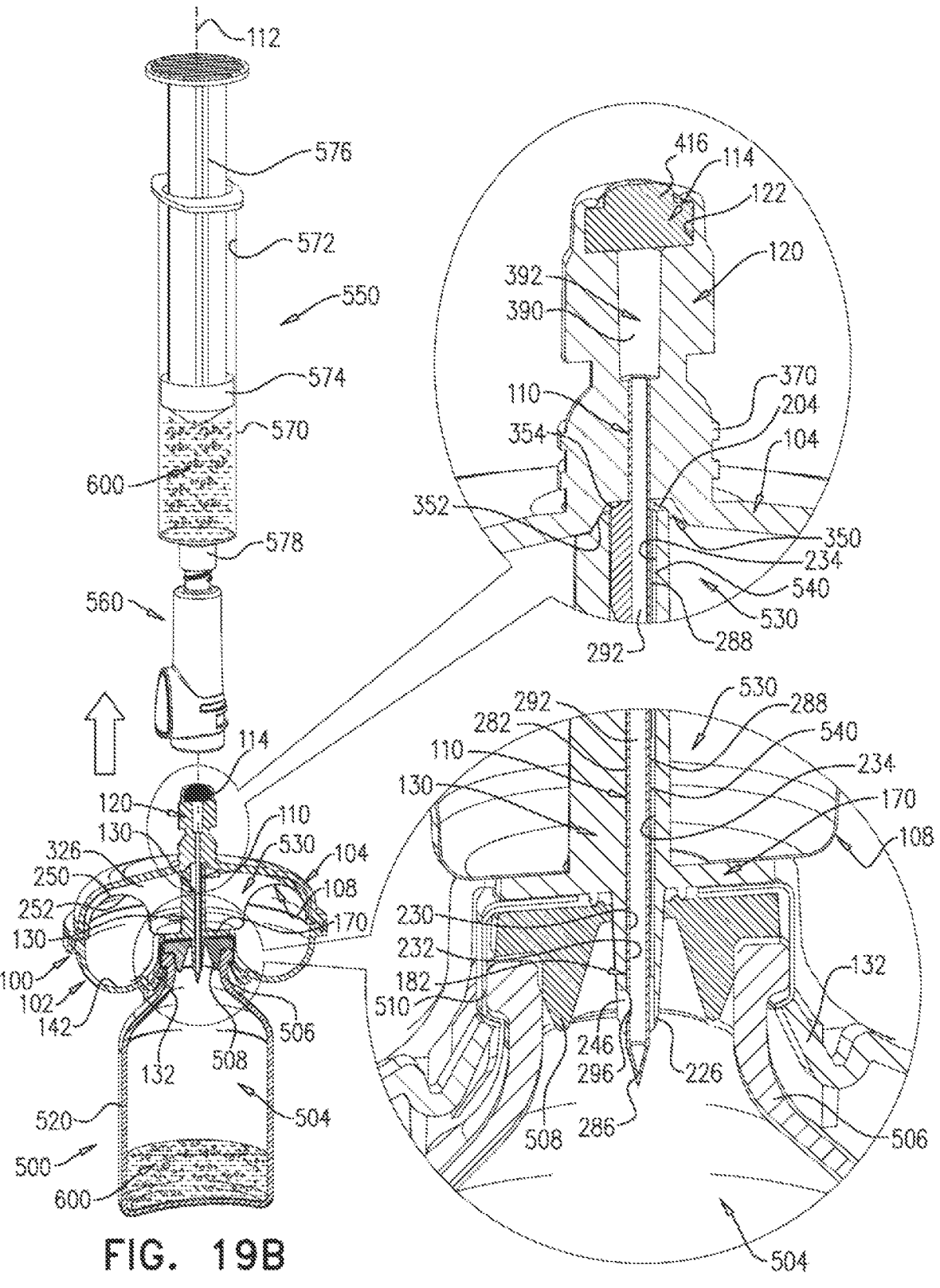

FIG. 1 is a simplified pictorial illustration of an assembled vial adaptor assembly for a closed fluid transfer system, constructed and operative in accordance with an embodiment of the present invention;

FIG. 2 is a simplified sectional illustration of the vial adaptor assembly of FIG. 1, FIG. 2 being taken along lines A-A in FIG. 1;

FIGS. 3A & 3B are simplified respective pictorial and sectional exploded view illustrations of the vial adaptor assembly of FIG. 1. FIG. 3B being taken along lines B-B in FIG. 3A;

FIGS. 4A & 4B are simplified respective pictorial upward facing and downward facing illustrations of a vial connector portion forming part of the vial adaptor assembly of FIG. 1;

FIG. 4C is a simplified top view illustration of the vial connector portion of FIGS. 4A & 4B;

FIGS. 4D & 4E are simplified respective sectional illustrations of the vial connector portion of FIGS. 4A & 4B, taken along mutually perpendicular section lines D-D and E-E in FIG. 4C;

FIGS. 5A & 5B are simplified respective pictorial and sectional illustrations of a deformable membrane forming pan of the vial adaptor assembly of FIG. 1, FIG. 5B being taken along lines B-B in FIG. 5A;

FIGS. 6A-6C are simplified respective pictorial, top view and sectional illustrations of a needle element forming part of the vial adaptor assembly of FIG. 1, FIG. 3C being taken along lines C-C in FIG. 6A;

FIGS. 7A & 7B are simplified respective pictorial and sectional illustrations of a syringe adaptor connector portion forming part of the vial adaptor assembly of FIG. 1, FIG. 7B being taken along lines B-B in FIG. 7A;

FIGS. 8A & 8B are simplified respective pictorial and sectional illustrations of a septum forming pan of the vial adaptor assembly of FIG. 1, FIG. 8B being taken along lines B-B in FIG. 8A;

FIGS. 9A & 9B are simplified respective pictorial and sectional illustrations of the vial adaptor assembly of FIG. 1, shown in a first operative orientation, where the vial adaptor assembly of FIG. 1 is about to be connected to a vial. FIG. 9B being taken along lines B-B in FIG. 9A;

FIGS. 10A & 10B are simplified respective pictorial and sectional illustrations of the vial adaptor assembly of FIG. 1, shown in a second operative orientation, where the vial adaptor assembly of FIG. 1 is connected to the vial. FIG. 10B being taken along lines B-B in FIG. 10A;

FIGS. 11A & 11B are simplified respective pictorial and sectional illustrations of the vial adaptor assembly of FIG. 1, shown in a third operative orientation, where the vial adaptor assembly of FIG. 1 and the vial are about to be connected to a syringe, having a syringe connector attached thereto, FIG. 11B being taken along lines B-B in FIG. 11A;

FIGS. 12A & 12B are simplified respective pictorial and sectional illustrations of the vial adaptor assembly of FIG. 1, shown in a fourth operative orientation, where the vial adaptor assembly of FIG. 1 and the vial are connected to the syringe through the syringe connector attached thereto, thus forming a closed fluid transfer system, FIG. 12B being taken along lines B-B in FIG. 12A:

FIGS. 13A & 13B are simplified respective pictorial and sectional illustrations of the vial adaptor assembly of FIG. 1, shown in a fifth operative orientation, where fluid is delivered from the syringe into the vial using the closed fluid transfer system, FIG. 13B being taken along lines B-B in FIG. 13A;

FIGS. 14A & 14B are simplified respective pictorial and sectional illustrations of the vial adaptor assembly of FIG. 1, shown in a sixth operative orientation, where the closed fluid transfer system composed of the vial adaptor assembly attached to both the vial and the syringe is inverted, such that the vial faces upwards, FIG. 14B being taken along lines B-B in FIG. 14A;

FIGS. 15A & 15B are simplified respective pictorial and sectional illustrations of the vial adaptor assembly of FIG. 1, shown in a seventh operative orientation, where fluid is drawn from the vial into the syringe using the closed fluid transfer system, FIG. 11B being taken along lines B-B in FIG. 15A;

FIGS. 16A & 16B are simplified respective pictorial and sectional illustrations of the vial adaptor assembly of FIG. 1, shown in an eighth operative orientation, where a relatively small amount of fluid is reprieved from the syringe into the vial using the closed fluid transfer system, FIG. 16B being taken along lines B-B in FIG. 16A;

FIGS. 17A & 17B are simplified respective pictorial and sectional illustrations of the vial adaptor assembly of FIG. 1, shown in a ninth operative orientation, where fluid is partially retrieved from the vial into the syringe using the closed fluid transfer system, FIG. 17B being taken along lines B-B in FIG. 17A;

FIGS. 18A & 18B are simplified respective pictorial and sectional illustrations of the vial adaptor assembly of FIG. 1, shown in a tenth operative orientation, where the required amount of fluid is retrieved from the vial into the syringe using the closed fluid transfer system, FIG. 18B being taken along lines B-B in FIG. 18A;

FIGS. 19A & 19B are simplified respective pictorial and sectional illustrations of the vial adaptor assembly of FIG. 1, shown in an eleventh operative orientation, where the syringe along with the syringe connector are disconnected from the vial adaptor assembly and the vial, FIG. 19B being taken along lines B-B in FIG. 19A.

DETAILED DESCRIPTION OF EMBODIMENTS OF INVENTION

Described below in accordance with an embodiment of the present invention is a vial adaptor assembly that is constructed and operative such that when connected to a vial at one side and to a syringe or other medical implement at another side, it enables a closed fluid transfer system. The closed fluid transfer system is configured for maintaining pressure equilibrium in-vial when drawing fluid therefrom or injecting fluid thereto and at the same time enabling safe handling of hazardous medications. It is a particular feature of an embodiment of the present invention that the entire amount of the medication contained within the closed fluid transfer system is utilized, preventing any wastage of medicament during the admixture process of the medication.

It is a further particular feature of an embodiment of the present invention that the vial adaptor assembly provides means for connection to a stopper of a vial. The vial adaptor assembly also provides a sealed access port with a pierceable septum, which is adapted to be connected to a syringe adaptor to allow a bi-directional passage of fluid. The vial adaptor assembly still further provides for means to eliminate pressure differences between the inner fluid pathways of the closed system and the ambient environment.

Reference is now made to FIG. 1, which is a simplified pictorial illustration of an assembled vial adaptor for a closed fluid transfer system, constructed and operative in accordance with an embodiment of the present invention. Reference is additionally made to FIG. 2, which a simplified sectional illustration of the vial adaptor of FIG. 1, FIG. 2 being taken along lines A-A in FIG. 1 and to FIGS. 3A & 3B, which are simplified respective pictorial and sectional exploded view illustrations of the vial adaptor of FIG. 1, FIG. 3B being taken along lines B-B in FIG. 3A.

A vial adaptor assembly 100 is seen in FIG. 1. The vial adaptor assembly 100 generally includes a vial connector portion 102, adapted to be securely attached to a syringe adaptor connector portion 104 and thus forming an enclosure volume 106 therebetween. A deformable membrane 108 is disposed within the enclosure volume 106 and is preferably fixedly attached in between the vial connector portion 102 and the syringe adaptor connector portion 104. A needle element 110 extends longitudinally along a longitudinal axis 112 from the syringe adaptor connector portion 104 to the vial connector portion 102. A septum element 114 is disposed within a portion of the syringe adaptor connector portion 104 and is configured for penetration thereof by a needle of a medical implement, which is adapted to engage the vial adaptor assembly 100.

It is seen particularly in FIGS. 3A & 38 that the syringe adaptor connector portion 104 of the vial adaptor assembly 100 is generally a dome-shaped element having a connection portion 120 extending upwardly therefrom along the longitudinal axis 112 and having a socket 122 configured for fitting of the septum element 114 therewithin, preferably by means of swaging.

It is further particularly seen in FIGS. 3A & 3B that the needle element 110 is hollow and arranged along the longitudinal axis 112.

The vial connector portion 102 of the vial adaptor assembly 100 is generally a concave element having an axially extending sheath 130 extending from a central location thereof generally along the longitudinal axis 112. The sheath 130 is configured for fixed fitting of the needle element 110 at least partially therethrough. The vial connector portion 102 additionally includes a plurality of circumferentially arranged snaps 132, adapted for fixed engagement with a medical implement, such as a vial.

Reference is now made to FIGS. 4A & 4B, which are simplified respective pictorial upward facing and downward facing illustrations of the vial connector portion 102 forming part of the vial adaptor assembly 100 of FIG. 1 and to FIG. 4C, which is a simplified top view illustration of the vial connector portion 102 of FIGS. 4A & 4B. Reference is additionally made to FIGS. 4D & 4E, which are simplified respective sectional illustrations of the vial connector portion 102 of FIGS. 4A & 4B, taken along mutually perpendicular section lines D-D and E-E in FIG. 4C.

The vial connector portion 102 is an integral part preferably made of plastic and arranged along longitudinal axis 112. It is seen in FIGS. 4A-4E that the vial connector portion 102 is generally concave and has a concave wall 140, with an inner surface 142 and an outer surface 144. A circumferential rim 146 extends radially outwardly from wall 140. A circumferential groove 148 is formed in the circumferential rim 146 and is disposed in between of two circumferential wall portions 150 and 152. It is seen in FIGS. 4A-4E that wall portion 150 has an upwardly facing edge 154 and a generally curved circumferential protrusion 156 is formed on the upwardly facing edge 154.

It is seen in FIGS. 4A, 4D and 4E that an upwardly extending protrusion 160 is formed at a central location of wall 140. The upwardly extending protrusion 160 has a plurality of radially spaced generally curved circumferential wall portions 162 forming gaps therebetween. An upper circumferential circular edge 164 is formed by site plurality of wall portions 162. The generally curved circumferential wall portion 162 has an inner wall surface 166 and an outer wall surface 168. A generally flat flange 170 is integrally formed within the circumference formed by the circumferential edge 164. Flange 170 has an upwardly facing surface 172 and a downwardly facing surface 174 having a generally circular downwardly facing protrusion 176 formed thereon. It is seen in FIGS. 4A, 4D and 4E that a generally curved circumferential protrusion 177 is formed on upwardly facing surface 172.

Sheath 130 has an upper sheath portion 180 extending upwardly from flange 170 and a spike portion 182 extending downwardly from flange 170. There are several generally curved wall portions 190 which surround spike portion 182 and are arranged circumferentially and spaced from each other. It is seen that snaps 132 are disposed in between of two neighboring curved wall portions 190 and extend slightly radially inwardly.

Several generally flat wall portions 192 extend radially inwardly from outer wall surface 168 and from curved wall portions 190 and circumferentially spaced from each other.

It is particularly seen in FIGS. 4A, 4C-4E that the upper sheath portion 180 has a generally cylindrical portion 200 with an outer surface 202 and an upwardly facing edge 204. Generally, three re-enforcing ribs 206 are arranged circumferentially and extend radially outwardly from the cylindrical portion 200, the ribs are radially spaced from each other. Preferably, each of the ribs 206 has an upwardly facing edge 208 disused along a plane that is generally parallel to the plane of upwardly facing edge 204 and an upwardly facing tapered edge 210 connecting edge 208 to edge 204. Ribs 206 extend from flange 170 to upwardly facing edge 204.

It is particularly seen in FIG. 4B that the spike portion 182 has a generally conical portion 220 with an outer surface 222 and a downwardly facing edge 224. A tapered circumferential wall surface 226 connects the downwardly facing edge 224 with the outer surface 222.

It is particularly seen in FIGS. 4D & 4E that a longitudinal bore 230 is formed through the sheath 130 and extends from upwardly facing edge 204 to downwardly facing edge 224. It is a particular feature of an embodiment of the present invention, as specifically seen in FIG. 4C, that bore 250 has a "drop" shape, having a w ide portion 232 and a narrow portion 234. A recess 236 extends radially outwardly from the wide portion 232 of the bore 230 and is oppositely directed with respect to the narrow portion 234 of the bore 230. The recess 236 extends longitudinally from the upwardly facing edge 204 downwardly along a portion of the longitudinal extent of she bore 230.

Bore 230 defines an inner surface 240 having an upper conical portion 242 and it bottom cylindrical portion 244. A generally U-shaped opening 246 is formed at the bottom end of the spike portion 182, adjacent downwardly facing edge 224 and is adapted to communicate with bore 230. The opening 246 is oriented at the same direction as recess 236, therefore opposite to the narrow portion 234 of bore 230.

Reference is now made to FIGS. 5A & 5B, which are simplified respective pictorial and sectional illustrations of the deformable membrane 108 forming part of the vial adaptor assembly 100 of FIG. 1, FIG. 5B being taken along lines B-B in FIG. 5A.

The deformable membrane 108 is an integral part, preferably made of plastic high-barrier laminate and arranged along longitudinal axis 112. It is seen in FIGS. 5A & 5B that the deformable membrane 108 is a deformable sheet of material having a pre-defined shape, and which is adapted to change its shape in response to pressure that is applied thereon. In FIGS. 5A & 5B the deformable membrane 108 is shown to have a generally concave shape corresponding to the inner surface 142 of the vial connector portion 102 and similarly corresponding to an inner surface of the syringe adaptor connector portion 104. The deformable membrane 108 has an upwardly facing surface 250 and a downwardly facing surface 252. The deformable membrane 108 further has a circumferential rim 254, having an upwardly facing edge 256 and a downwardly facing edge 258. The deformable membrane 108 has a centrally located depression 260, having an upwardly facing surface 262, a downwardly facing surface 264 and a centrally located aperture 266.

Reference is now made to FIGS. 6A-6C, which are simplified respective pictorial, top view and sectional illustrations of the needle element 110 forming part of the vial adaptor assembly 100 of FIG. 1. FIG. 3C being taken along lines C-C in FIG. 6A.

The needle element 110 is a generally hollow cylindrical integral part, preferably made of metal and arranged along the longitudinal axis 112. The needle element 110 has a cylindrical portion 282 with an upwardly facing edge 281 at one end thereof and a sharp conical up 286 at the other end. The needle element 110 has an outer surface 288 and an inner surface 290, defining an interior fluid passage, which serves as a liquid pathway 292. If is noted that the liquid pathway 292 extends generally along the longitudinal axis 112.

It is seen that a fin 294 extends generally radially outwardly from cylindrical portion 282. The fin 294 has an upwardly facing edge 295. It is further seen that an opening 296 is formed in the cylindrical portion 282 and communicates with the liquid pathway 292. The opening 296 is disposed adjacent the tip 286 of needle element 110 and is oriented at the same direction as the fin 294.

Reference is now made to FIGS. 7A & 7B, which are simplified respective pictorial and sectional illustrations of the syringe adaptor connector portion 104 forming part of the vial adaptor assembly 100 of FIG. 1, FIG. 7B being taken along lines B-B in FIG. 7A.

As noted above, the syringe adaptor connects portion 104 of the vial adaptor assembly 100 is generally a dome-shaped element having connection portion 120 extending upwardly therefrom along the longitudinal axis 112 and having socket 122 configured for fitting of the septum element 114 therewithin preferably by means of swaging.

It is seen in FIGS. 7A & 7B that the dome-shaped syringe adaptor connector portion 104 has a generally curved wall 320, having a flat annular wall portion 322 at one end which connects the curved wall 320 with the connection portion 120. The curved wall 320 has an outer surface 324 and an inner surface 326. A radially outwardly extending circumferential rim 328 is formed at another end of the curved wall 320. A downwardly facing tongue 330 extends downwardly from circumferential rim 328 and generally perpendicularly thereto.

It is seen particularly in FIG. 7B that a plurality of circumferentially spaced apart grooves 340 are formed on a portion of the inner surface 326 of the syringe adaptor connector portion 104. The grooves 340 generally extend upwardly from a location adjacent the circumferential rim 328. A generally smooth surface 342 extends from the upward end of the grooves 340 towards a central top location on the inner surface 326 of the syringe adaptor connector portion 104, terminating at an upwardly protruding liquid medicament collecting and draining well 350, located at the apex of the dome-shaped syringe adaptor connector portion 104. The liquid medicament collecting and draining well 350 has a tapered wall surface 352 and a flat downwardly facing surface 354 and it is specifically seen in FIG. 7B that the liquid medicament collecting and draining well 350 is generally centered along the longitudinal axis 112.

The connection portion 120 has a bottom portion 360, an intermediate portion 362 and an upper portion 364. The bottom portion 360 includes a series of longitudinally spaced flanges 370 having outer circumferential edges 372. A neck portion 374 extends upwardly from the uppermost flange 370 and connects the bottom portion 360 to the intermediate portion 362. The intermediate portion 362 is generally cylindrical portion having a first outer diameter, and having a downwardly facing shoulder 376 adjacent the neck portion 374. A tapered wall surface 378 connects the intermediate portion 362 with an upper portion 364.

The upper portion 364 is generally cylindrical portion having a second outer diameter, which is generally smaller than the first outer diameter. The upper portion 364 has an upwardly facing circumferential edge 380.

A through bore 390 is formed through the connecting portion 120 and has several different portions, each having a different diameter. The bore 390 extends longitudinally along longitudinal axis 112. The upper portion of the through bore 390 is socket 122, having a first diameter and extending through the longitudinal extent of the upper portion 364. An intermediate bore 392 extends downwardly longitudinally from the socket 122 to a location adjacent the neck portion 374. The intermediate bore 392 has a second diameter, which is generally smaller than the first diameter of socket 122. A bottom bore 394 extends downwardly longitudinally from the intermediate bore 392 to downwardly facing surface 354 of liquid medicament collecting and draining well 350, forming an aperture 400 in the downwardly facing surface 354 and thereby communicating with the liquid medicament collecting and draining well 350. The bottom bore 394 has a third diameter, which is generally smaller than the second diameter of the intermediate bore 392.

Reference is now made to FIGS. 8A & 8B, which are simplified respective pictorial and sectional illustrations of the septum 114 forming part of the vial adaptor assembly 100 of FIG. 1, FIG. 8B being taken along lines B-B in FIG. 8A.

The septum 114 is a disc shaped integral solid part, preferably made of rubber and arranged having longitudinal axis 112. The septum 114 has an upwardly facing surface 410, a downwardly fitting surface 412 and an outer facing circumferential surface 414. An upwardly facing protrusion 416 is formed on the upwardly facing surface 410.

Reference is now made to FIGS. 9A & 9B, which are simplified respective pictorial and sectional illustrations of the vial adaptor assembly 100 of FIG. 1, shown in a first operative orientation, where the vial adaptor assembly 100 of FIG. 1 is about to be connected to a vial, FIG. 9B being taken along lines B-B in FIG. 9A.

It is seen in FIGS. 9A & 9B that the vial adaptor assembly 100 as described with reference to FIGS. 1-8B is about to be connected to a vial 500. The vial 500 has a barrel 502 having an inner volume 504 and a neck portion 506 defining an opening covered by septum 508 and fixed in place by an aluminum retaining collar 510. The vial 500 is adapted to contain a drug powder 520 within its inner volume 504 in this operative orientation.

It is seen specifically in FIG. 9B that the outer portion of the deformable membrane 108 is fixedly connected to vial connector portion 102 by means of ultrasonic welding of rim 254 of the deformable membrane 108 with circumferential rim 146 of the vial connector portion 102, more specifically the connection is formed between the downwardly facing edge 258 of the deformable membrane 108 and the circumferential protrusion 156 of the vial connector portion 102.

The inner portion of the deformable membrane 108 is fixedly connected to the vial connector portion 102 by means of ultrasonic welding of centrally located depression 260 of the deformable membrane 108 with flat flange 170 of the vial connector portion 102, more specifically the connection is formed between the downwardly facing surface 264 of the deformable membrane 108 and the circumferential protrusion 177 of the vial connector portion 102.

It is further seen in FIG. 9B that syringe adaptor connector portion 104 is fixedly connected to the vial connector portion 102 by means of ultrasonic welding of downwardly facing tongue 330 or syringe adaptor connector portion 104 which is inserted into the circumferential groove 148 of the vial connector portion 102.

It is seen that a portion of axially extending sheath 130 is extending through aperture 266 of the deformable membrane 108.

It is seen that a pressure equalization chamber 530 is formed between the deformable membrane 108 and the syringe adaptor connector portion 104, and it is noted that in this operative orientation shown in FIGS. 9A & 9B, the volume of the pressure equalization chamber 530 is minimal, due to the fact that the upwardly facing surface 250 of the deformable membrane 108 is mostly positioned adjacent the grooves 342 formed on the inner surface 326 of the syringe adaptor connector portion 104 and the downwardly facing surface 252 of the deformable membrane 108 is spaced apart from the inner surface 142 of the vial connector portion 102. The pressure equalization chamber 530 is empty of fluid as shown in this operative orientation.

It is a particular feature of an embodiment of the present invention that the pressure equalization chamber 530 contains the liquid medicament collecting and draining well 350 therewithin, whereas a direct fluid communication is permitted between the pressure equalization chamber 530 and the venting pathway 540 via the liquid medicament collecting and draining well 350.

Septum 114 is inserted into socket 22 of she syringe adaptor connector portion 104 and the upper end of the upper portion 364 of the connection portion 120 of the syringe adaptor connector portion 104 is folded during swaging process such as to firmly hold the septum 114 within the syringe adaptor connector portion 104 by engagement of the upper portion 364 with the upwardly facing surface 410 of the septum 114. Upwardly facing protrusion 416 of the septum 114 is exposed for enabling penetration thereof by a needle of a syringe adapter, as described in detail hereinbelow.

The upwardly facing tapered edge 210 of the upper sheath portion 180 abuts the tapered wall surface 352 of the liquid medicament collecting and draining well 350 of the syringe adaptor connector portion 104.

It is further seen in FIG. 9B that cylindrical portion 282 of the needle element 110 is inserted into the bottom bore 394, which is formed within the connection portion 120 of the syringe adaptor connector portion 104 and is firmly held therewithin either by adhesive or by heat welding. It is seen that the upwardly facing edge 295 of fin 294 of the needle element 110 preferably abuts the downwardly facing surface 354 of the liquid medicament collecting and draining well 350 of the syringe adaptor connector portion 104.

The cylindrical portion 282 of the needle element 110 is further inserted through bore 230 formed within sheath 130. It is a particular feature of an embodiment of the present invention that the needle element 110 is inserted into the wide portion 232 of bore 230, thus forming a venting pathway 540 extending through the narrow portion 231 of the bore 230. The venting pathway 540 is located between the outer surface 288 of the needle element 110 and the inner surface 240 defined by bore 230 and thus at least partially surrounds the liquid pathway 292, which extends within the needle element 110. The outer surface 288 of the needle element 110 is circumferentially enclosed by the wide portion 232 of bore 230.

It is seen in FIG. 9B that the fin 294 of the needle dement 110 is disposed within recess 236 formed within bore 230 of the sheath 130. The fin 294 is adapted to orient the needle element 110 such that opening 296 of the needle element 110 and U-shaped opening 246 of the spike portion 182 are facing the same direction.

It is further seen in FIG. 9B that sharp conical tip 286 of the needle element 110 slightly protrudes downwardly from the tapered circumferential wall surface 226 of the spike portion 182 and together therewith forms a sharp tip, which is adapted for penetrating septum 508 of vial 500.

Spike portion 182 of the sheath 130 and the sharp conical tip 286 of the needle element 110 are circumferentially surrounded by snaps 132 of the vial connector portion 102.

It is noted that the vial adaptor assembly 100 is generally axially symmetric about longitudinal axis 112.

Reference is now made to FIGS. 10A & 10B, which are simplified respective pictorial and sectional illustrations of the vial adaptor assembly 100 of FIG. 1, shown in a second operative orientation, where the vial adaptor assembly 100 of FIG. 1 is connected to the vial 500, FIG. 10B being taken along lines B-B in FIG. 10A.

It is appreciated that all spatial relationships between the various components of the vial adaptor assembly 100, as described with reference to FIGS. 9A & 9B remain unchanged and additional relationships between the vial adaptor assembly 100 and the vial 500 now exist in this second operative orientation shown in FIGS. 10A & 10B, as described in detail hereinbelow.

It is seen in FIG. 10B that upon attachment of the vial adaptor assembly 100 to the vial 500, sheath 130 penetrates the septum 508 of the vial 500, such that the spike portion 182 of the sheath 130 and the sharp conical tip 286 of the needle element 110 are now disposed within the inner volume 504 of the vial 500. It is noted that both opening 206 of the needle element 110 and the U-shaped opening 246 of the spike portion 182 are now disposed within the inner volume 504 of the vial 500.

It is further seen in FIG. 10B that flat wall portions 192 of the vial connector portion 102 radially engage the retaining collar 510 of the vial 500 to provide for stable connection between the vial adaptor assembly 100 and the vial 500. Downwardly facing protrusion 176 of the vial connector portion 102 engages the septum 508 of the vial 500 for the same purpose.

The vial adaptor assembly 100 is fixedly and irremovably attached to the vial 500 by means of locking engagement of snaps 132 of the vial connector portion 102 with the neck portion 506 and with the retaining collar 510 of the vial 500.

Reference is now made to FIGS. 11A & 11B, which are simplified respective pictorial and sectional illustrations of the vial adaptor assembly 100 of FIG. 1, shown in a third operative orientation, where the vial adaptor assembly 100 of FIG. 1 and the vial 500 are about to be connected to a syringe, having a syringe connector attached thereto. FIG. 11B being taken along lines B-B in FIG. 11A.

It is appreciated that all spatial relationships between the various components of the vial adaptor assembly 100, as described with reference to FIGS. 10A & 10B remain unchanged other than mentioned below and additional relationships between the vial adaptor assembly 100 and the vial 500 and between a syringe 550 and a syringe adaptor 560 now exist in this third operative orientation shown in FIGS. 11A & 11B, as described in detail hereinbelow.

It is seen in FIGS. 11A & 11B that the syringe 550 is attached to the syringe adaptor 560, the syringe adaptor 560 that is used in accordance with an embodiment of the present invention is such as the Onguard® syringe adaptor, commercially available from B. Braun of Bethlehem, Pennsylvania USA.

The syringe 550 has a band 570 having an inner volume 572, which is confined at one end by a piston 574 which is fixedly connected or integrally made with a plunger rod 576 that is slidable relative to the barrel 570. The syringe 550 has a liter 578 at another end thereof, which is adapted to be threadably attached to the syringe adaptor 560. It is noted that the syringe 550 contains a diluent 580 within the inner volume 572 of the barrel 570.

It is seen in FIGS. 11A & 11B that the syringe 550, which is connected to the syringe adaptor 560 is about to be connected to the vial adaptor assembly 100, which was previously connected to vial 500, as described with reference to FIGS. 10A & 10B.

Reference is now made to FIGS. 12A & 12B, which are simplified reflective pictorial and sectional illustrations of the vial adaptor assembly 100 of FIG. 1, shown in a fourth operative orientation, where the vial adaptor assembly 100 of FIG. 1 and the vial 500 are connected to the syringe 550 through the syringe connector 560 attached thereto, thus forming a closed fluid transfer system, FIG. 12B being taken along lines B-B in FIG. 12A.

It is appreciated that all spatial relationships between the various components of the vial adaptor assembly 100, as described with reference to FIGS. 10A & 10B remain unchanged other than mentioned below. Additional relationships between the vial adaptor assembly 100 and the vial 500 and between the syringe 550 and the syringe adaptor 560 now exist in this fourth operative orientation shown in FIGS. 12A & 12B, as described in detail hereinbelow.

It is seen in FIGS. 12A & 12B that the syringe adaptor 560, which is connected to the syringe 550, as shown in FIGS. 11A & 11B, is now connected to the vial adaptor assembly 100. It is seen that the syringe adaptor 560 includes an outer surface 590, and inner surface 592 and a downwardly facing edge 594. A syringe adaptor needle 596 is contained within the syringe adaptor 560.

The syringe adaptor 560 is attached to the connection portion 120 of the syringe adaptor connector portion 104, such that connection portion 120 of the syringe adaptor connector portion 104 is contained within the inner volume of the syringe adaptor 560 and a snap 598 which is radially inwardly extending from the inner surface 592 of the syringe adaptor 560 is adapted to be locked against site downwardly facing shoulder 326 of the syringe adaptor connector portion 104. The inner surface 592 of the syringe adaptor 560 engages flanges 370 of the syringe adaptor connector portion 104 to provide stable connection between the syringe adaptor connector portion 104 and the syringe adaptor 560. The downwardly facing edge 594 of the syringe adaptor 560 is disposed in vicinity of annular wall portion 322 of the syringe adaptor connector portion 104.

It is seen particularly in FIG. 12B that the syringe adaptor needle 596 penetrates the septum 114 and extends into the intermediate bore 392 of through bore 390 of the syringe adaptor connector portion 104, thereby creating a fluid passage from the inner volume 572 of the syringe 550, through the syringe adaptor needle 596, via the liquid pathway 292 of the needle element 110 and into the inner volume 504 of the vial 500 via opening 296 at the tip 286 of the needle element 110, which is located within this inner volume 504.

Reference is now made to FIGS. 13A & 13B, which are simplified respective pictorial and sectional illustrations of the vial adaptor assembly 100 of FIG. 1, shown in a fifth operative orientation, where fluid is delivered from the syringe 550 into the vial 500 using the closed fluid transfer system, FIG. 13B being taken along lines B-B in FIG. 13A.

It is appreciated that all spatial relationships between the various components of the vial adaptor assembly 100, its described with reference to FIGS. 10A & 10B remain unchanged other than mentioned below, relationships between the adaptor assembly 100 and the vial 500 and between the syringe 550 and the syringe adaptor 560, as described with reference to FIGS. 12A & 12B remain unchanged other than mentioned below. Additional relationships between the vial adaptor assembly 100 and the vial 500 and between the syringe 550 and the syringe adaptor 560 now exist in this fifth operative orientation shown in FIGS. 13A & 13B, as described in detail hereinbelow.

It is seen in FIGS. 13A & 13B that the plunger rod 576 of the syringe 550 is pushed inwardly into barrel 570 of the syringe 550 by the user, such that the plunger rod 576 slides relative to barrel 570 of the syringe 550 and thus expels the diluent 580 contained within the inner volume 572 of the syringe 550 through the needle 596 of the syringe adaptor 560 into the needle element 110 of the vial adaptor assembly 100 and further into the inner volume 504 of the vial 500, whereas the diluent 580 is mixed with the drug powder 520 and forms a fluid drug mixture 600. The plunger rod 576 is shown in FIGS. 13A & 13B in the process or expelling diluent 580 out of the barrel 570 of the syringe 550.

It is specifically seen in FIG. 13B that the diluent 580 is forced from the barrel 570 of the syringe 550 into the inner volume of the needle 596 of the syringe adaptor 560, and further flows through intermediate bore 392 of the syringe adaptor connector portion 104 into the liquid pathway 292 of the needle element 110 and enters the inner volume 504 of the vial 500 through opening 296 of the needle element 110 and further through U-shaped opening 246 of the spike portion 182.

It is a particular feature of an embodiment of the present invention that due to the passage of diluent into the inner volume 504 of the vial 500, the pressure within the vial 500 is increased and thus urges passage of air, indicated by arrow 602 in FIG. 13B, from the inner volume 504 of the vial 500 into pressure equalization chamber 530 formed between the deformable membrane 108 and the syringe adaptor connector portion 104, thus causing deformation of the shape of the membrane 108, such that it is now inverted.

It is seen that the volume of the pressure equalization chamber 530 is now increased in comparison to the volume of pressure equalization chamber 530 as shown in FIG. 9B, due to the fact that air passed from the inner volume 504 of the vial 500 into the pressure equalization chamber 530, as indicated by arrow 602, causing deformation of the membrane 108, such that the upwardly facing surface 250 of the deformable membrane 108 is spaced apart from the grooves 342 formed on the inner surface 326 of the syringe adaptor connector portion 104 and the downwardly facing surface

252 of the deformable membrane 508 is mostly disposed adjacent the inner surface 142 of the vial connector portion 102.

It is specifically seen in FIG. 13B that air passes from the inner volume 504 of the vial 500 and flows into venting pathway 540, formed between the outer surface 288 of the needle element 110 and the narrow portion 234 of bore 250 of the sheath 130 and enters the pressure equalization chamber 530 through the gap formed between upwardly facing edge 204 of sheath 130 of the vial connector portion 102 and between liquid medicament collecting and draining well 350 of the syringe adaptor connector portion 104.

It is a particular feature of an embodiment of the present invention that increasing the pressure within the vial 500 urges transfer of fluid from the vial 500 into the pressure equalization chamber 530 and decreasing pressure within the vial 500 urges transfer of fluid from the pressure equalization chamber 530 into the vial 500.

Reference is now made to FIGS. 14A & 14B, which are simplified respective pictorial and sectional illustrations of the vial adaptor assembly 100 of FIG. 1, shown in a sixth operative orientation, where the closed fluid transfer system composed of the vial adaptor assembly 100 attached to both the vial 500 and the syringe 550 is inverted, such that the vial 500 faces upwards, FIG. 14B being taken along lines B-B in FIG. 14A.

It is appreciated that all spatial relationships between the various components of the vial adaptor assembly 100 as described with reference to FIGS. 10A & 10B remain unchanged other than mentioned below, relationships between the adaptor assembly 100 and the vial 500 and between the syringe 550 and the syringe adaptor 560, as described with reference to FIGS. 13A & 13B remain unchanged other than mentioned below. Additional relationships between the vial adaptor assembly 100 and the vial 500 and between the syringe 550 and the syringe adaptor 560 now exist in this sixth operative orientation shown in FIGS. 14A & 14B, as described in detail hereinbelow.

It is seen in FIGS. 14A & 14B that the closed fluid transfer system, including the vial 500, vial adaptor assembly 100, syringe adaptor 560 and syringe 550 all connected to each other, is flipped in order to aspirate fluid drug mixture 600 from the inner volume 504 of the vial 500 into the syringe 550.

It is seen that in this operative orientation the syringe 550 is empty and the sharp conical tip 286 of needle element 110 is submerged within fluid drug mixture 600, such that both opening 296 of the needle element 110 and U-shaped opening 246 of the spike portion 182 are submerged within the fluid drug mixture 600.

Reference is now made to FIGS. 15A & 15B, which are simplified respective pictorial and sectional illustrations of the vial adaptor assembly 100 of FIG. 1, shown in a seventh operative orientation, where fluid is drawn from the vial 500 into the syringe 550 using the closed fluid transfer system. FIG. 15B being taken along lines B-B in FIG. 15A.

It is appreciated that all spatial relationships between the various components of the vial adaptor assembly 100, as described with reference to FIGS. 10A & 10B remain unchanged other than mentioned below, relationships between the adaptor assembly 100 and the vial 500 and between the syringe 550 and the syringe adaptor 560, as described with reference to FIGS. 14A & 14B remain unchanged other than mentioned below. Additional relationships between the vial adaptor assembly 100 and the vial 500 and between the syringe 550 and the syringe adaptor 560 now exist in this seventh operative orientation shown in FIGS. 15A & 15B, as described in detail hereinbelow.

It is seen in FIGS. 15A & 15B that the plunger rod 576 of the syringe 550 is pulled outwardly relative to barrel 570 by the user, such that the plunger rod 576 slides relative to barrel 570 of the syringe 550 and thus the fluid drug mixture 600 contained within the inner volume 504 of the vial 500 is aspirated through the needle element 110 of the vial adaptor assembly 100 into the needle 596 of the syringe adaptor 560 and further into the inner volume 572 of the syringe 550. The plunger rod 576 is shown in FIGS. 15A & 15B in the process of aspirating fluid drug mixture 600 into the barrel 570 of the syringe 550.

It is specifically seen in FIG. 15B that the fluid drug mixture 600 is aspirated from the inner volume 504 of the vial 500 through opening 296 of the needle element 110 and further through U-shaped opening 246 of the spike portion 182 and into the liquid pathway 292 of the needle element 110 and further flows through intermediate bore 392 of the syringe adaptor connector portion 104 into the inner volume of the needle 596 of the syringe adaptor 560 and further into barrel 570 of the syringe 550.

It is a particular feature of an embodiment of the present invention that due to the aspiration of fluid drug mixture 600 out of the inner volume 504 of the vial 500, the pressure within the vial 500 is decreased and thus urges passage of air, indicated by arrow 602 in FIG. 15B, from the pressure equalization chamber 530 formed between the deformable membrane 108 and the syringe adaptor connector portion 104 into the inner volume 504 of the vial 500, thus causing deformation of the shape of the membrane 108, such that it is now inverted.

It is seen that the volume of the pressure equalization chamber 530 is now decreased in comparison to the volume of pressure equalization chamber 530 as shown in FIG. 13B, due to the fact that air passed from the pressure equalization chamber 530 into the inner volume 504 of the vial 500, as indicated by arrow 602, causing deformation of the membrane 108, such that the upwardly facing surface 250 of the deformable membrane 108 is mostly disposed adjacent the grooves 342 formed on the inner surface 326 of the syringe adaptor connector portion 104 and the downwardly facing surface 252 of the deformable membrane 108 is spaced apart from the inner surface 142 of the vial connector portion 102.

It is specifically seen in FIG. 15B that air passes, as indicated by arrow 602, from the pressure equalization chamber 530 through the gap formed between upwardly facing edge 204 of sheath 130 of the vial connector portion 102 and between liquid medicament collecting and draining well 350 of the syringe adaptor connector portion 104 and flows into venting pathway 540, formed between the outer surface 288 of the needle element 110 and the narrow portion 234 of bore 230 of the sheath 130 and into the inner volume 504 of the vial 500.

It is a particular feature of an embodiment of the present invention that increasing the pressure within the vial 500 urges transfer of fluid from the vial 300 into the pressure equalization chamber 530 and decreasing pressure within the vial 500 urges transfer of fluid from the pressure equalization chamber 530 into the vial 500.

Reference is now made to FIGS. 16A & 16B, which are simplified respective pictorial und sectional illustrations of the vial adaptor assembly 100 of FIG. 1, shown in an eighth operative orientation, where a relatively small amount of fluid is retrieved from the syringe 550 into the vial 500 using the closed fluid transfer system. FIG. 16B being taken along lines B-B in FIG. 16A.

It is appreciated that all spatial relationships between the various components of the vial adaptor assembly 100, as described with reference to FIGS. 10A & 10B remain unchanged other than mentioned below, relationships between the adaptor assembly 100 and the vial 500 and between the syringe 550 and the syringe adaptor 560, as described with reference to FIGS. 15A & 15B remain unchanged other than mentioned below. Additional relationships between the vial adaptor assembly 100 and the vial 500 and between the syringe 550 and the syringe adaptor 560 now exist in this eighth operative orientation shown in FIGS. 16A & 16B, as described in detail hereinbelow.

FIGS. 16A & 16B illustrate a situation where an excessive amount of fluid drug mixture 600 was aspirated from the vial 500 into the syringe 550 and in this operative orientation shown in FIGS. 16A & 16B, the user retrieves a small amount of fluid drug mixture 600 back from the syringe 550 into the inner volume 504 of the vial 500. Alternatively, it may be required to retrieve a small amount of fluid, such as air, buck from the syringe 550 into the inner volume 504 of the vial 500 in case air was inadvertently aspirated from the vial 500 into the syringe 550.

It is seen in FIGS. 16A & 16B that the plunger rod 576 of the syringe 350 is pushed inwardly by the user, such that the plunger rod 576 slides relative to barrel 570 of the syringe 550 and thus expels a small amount of fluid drug mixture 600 from the syringe 550 through the needle 596 of the syringe adaptor 560 into the needle element 110 of the vial adaptor assembly 100 and further into the inner volume 504 of the vial 500. The plunger rod 576 is shown in FIGS. 16A & 16B in the process of expelling a portion of the fluid drug mixture 600 out of the barrel 570 of the syringe 550.

It is specifically seen in FIG. 16B that a first portion of the fluid drug mixture 600 is forced from the barrel 570 of the syringe 550 into the inner volume of the needle 596 of the syringe adaptor 560, and further flows through intermediate bore 392 of the syringe adaptor connector portion 104 into the liquid pathway 292 of the needle element 110 and enters the inner volume 504 of the vial 500 through opening 296 of the needle element 110 and further through U-shaped opening 246 of the spike portion 182.

It is seen particularly in FIG. 16B that upon returning of the fluid drug mixture 600 into the inner volume 501 of the vial, and due to the fact that the spike portion 182 is submerged within fluid drug mixture 600, a second portion of the fluid drug mixture 600 contained in the inner volume 504 of the vial 500 is pushed into pressure equalization chamber 530 formed between the deformable membrane 108 and the syringe adaptor connector portion 104 due to increase of pressure within the vial 500. It is particularly seen that this second portion of fluid drag mixture 600 dial is pushed into pressure equalization chamber 530 flows from the inner volume 504 of the vial 500 and flows info venting pathway 540, formed between the outer surface 288 of the needle element 110 and the narrow portion 234 of bore 230 of the sheath 130 and enters the pressure equalization chamber 530 via the gap formed between upwardly facing edge 204 of sheath 130 of the vial connector portion 102 and between liquid medicament collecting and draining well 350 of the syringe adaptor connector portion 104. It is seen that the second portion of the fluid drug mixture 600 is accumulated within the pressure equalization chamber 530, and specifically within liquid medicament collecting and draining well 350 of the syringe adaptor connector portion 104 in this operative orientation. It is noted that air remains within the vial 500 in this operative orientation.

It is seen that the volume of the pressure equalization chamber 530 is now increased in comparison to the volume of pressure equalization chamber 530 as shown in FIG. 15B, due to the fact that fluid drug mixture 600 passed from the inner volume 504 of the vial 500 into the pressure equalization chamber 530, as indicated by arrow 600, causing deformation of the membrane 108, such that the upwardly facing surface 250 of the deformable membrane 108 is spaced apart from the grooves 342 formed on the inner surface 326 of the syringe adaptor connector portion 104 and the downwardly facing surface 232 of the deformable membrane 108 is mostly disposed adjacent the inner surface 142 of the vial connector portion 102.

It is a particular feature of an embodiment of the present invention that increasing the pressure within the vial 500 urges transfer of fluid from the vial 500 into the pressure equalization chamber 530 and decreasing pressure within the vial 500 urges transfer of fluid from the pressure equalization chamber 530 into the vial 500.

Reference is now made to FIGS. 17A & 17B, which are simplified respective pictorial and sectional illustrations of the vial adaptor assembly 100 of FIG. 1, shown in a ninth operative orientation, where fluid is partially retrieved from the vial 500 into the syringe 550 using the closed fluid transfer system, FIG. 17B being taken along lines B-B in FIG. 17A.

It is appreciated thru all spatial relationships between the various components of the vial adaptor assembly 100, as described with reference to FIGS. 10A & 10B remain unchanged other than mentioned below, relationships between the adaptor assembly 100 and the vial 500 and between the syringe 550 and the syringe adaptor 560, as described with reference to FIGS. 16A & 16B remain unchanged other than mentioned below. Additional relationships between the vial adaptor assembly 100 and the vial 500 and between the syringe 550 and the syringe adaptor 560 now exist in this ninth operative orientation shown in FIGS. 17A & 17B, as described in detail hereinbelow.

It is seen in FIGS. 17A & 17B that the plunger rod 576 of the syringe 550 is pulled outwardly by the user, such that the plunger rod 576 slides relative to barrel 570 of the syringe 550 and thus a portion of the fluid drug mixture 600 contained within the inner volume 504 of the vial 500 is aspirated through the needle element 110 of the vial adaptor assembly 100 into the needle 596 of the syringe adaptor 560 and further into the inner volume 572 of the syringe 550. The plunger rod 576 is shown in FIGS. 17A & 17B in the process of aspirating fluid drug mixture 600 into the barrel 570 of the syringe 550.

It is specifically seen in FIG. 17B that the fluid drug mixture 600 is aspirated from the inner volume 504 of the vial 500 through opening 296 of the needle element 110 and further through U-shaped opening 246 of the spike portion 182 and into the liquid pathway 292 of the needle element 110 and further flows through intermediate bore 392 of the syringe adaptor connector portion 104 into the inner volume of the needle 596 of the syringe adaptor 560 and further into barrel 570 of the syringe 550. Aspiration of fluid drug mixture 600 puts the entire inner volume of the system under vacuum.

It is a particular feature of an embodiment of the present invention that in this operative orientation, the spike portion 182 of the vial connector position 102 is submerged within the fluid drug mixture 600. Due to the aspiration of fluid drug mixture 600 out of the inner volume 504 of the vial 500, the pressure within the vial 500 is decreased and vacuum is created, thus urges passage of the second portion of fluid drug mixture 600 which accumulated within pressure equalization chamber 530 as shown and described with reference to FIG. 16B, from the pressure equalization chamber 530 formed between the deformable membrane 108 and the syringe adaptor connector portion 104 into the inner volume 504 of the vial 500, thus causing deformation of the shape of the membrane 108, such that it is now inverted and the pressure equalization chamber 530 is disposed in its minimal volume.

It is noted that when the pressure equalization chamber 530 is in its minimal volume, the deformable membrane 108 is pushed against the inner surface 326 of the syringe adaptor connector portion 104. Grooves 342 are used to prevent fluid entrapment between the deformable membrane 108 and the inner surface 326 of syringe adaptor connector portion 104. When the system is uric mated such as shown in FIGS. 17A & 17B, gravity causes the fluid to be collected within the pressure equalization chamber 530 and vacuum from the syringe 550 urges the fluid drug mixture 600 upwardly bock into the vial 500 and then in turn into the syringe 550 via liquid pathway 292 of the vial adaptor assembly 100.

It is seen that the volume of the pressure equalization chamber 530 is now decreased in comparison to the volume of pressure equalization chamber 530 as shown in FIG. 16B, due to the fact that a portion of the fluid drug mixture 600 passed from the pressure equalization chamber 530 into the inner volume 504 of the vial 500, causing deformation of the membrane 108, which compensates for the vacuum that is created in the pressure equalization chamber 530, such that the upwardly facing surface 250 of the deformable membrane 108 is mostly disposed adjacent the grooves 342 formed on the inner surface 326 of the syringe adaptor connector portion 104 and the downwardly facing surface 252 of the deformable membrane 108 is spaced apart from the inner surface 142 of the vial connector portion 102.

It is specifically seen in FIG. 17B that the fluid drug mixture 600 flows upwardly from the pressure equalization chandler 530 through the gap formed between upwardly facing edge 204 of sheath 130 of the vial connector portion 102 and between liquid medicament collecting and draining well 350 of the syringe adaptor connector portion 104 and flows into venting pathway 540, formed between the outer surface 288 of the needle element 110 and the narrow portion 234 of bore 230 of the sheath 130 and into the inner volume 504 of the vial 500. The amount of air within the vial 500 remains unchanged in this operative orientation.

It is a particular feature of an embodiment of the present invention that the fluid drug mixture 600 that becomes located within the pressure equalization chamber 530 during injection of the fluid drug mixture 600 back into the vial 500 is collected within the collecting and draining well 350 due to the geometry of the syringe adaptor connector portion 104 forming the liquid medicament collecting and draining well 350 at the bottom of the pressure equalization chamber 530 and due to the pressure differential between the pressure equalization chamber 530 and the inner volume 504 of the vial 500. It is specifically noted that the liquid medicament collecting and draining well 350 is formed by the tapered wall surface 352 and the flat downwardly facing surface 354.

The plunger rod 576 in shown in the process of aspirating the required amount of fluid drug mixture 600 into the syringe 550, thus a portion of the fluid drug mixture 600 still remains within pressure equalization chamber 530, as shown in this operative orientation.

It is a particular feature of an embodiment of the present invention that increasing the pressure within the vial 500 urges transfer of fluid from the vial 500 into the pressure equalization chamber 530 and decreasing pressure within the vial 500 urges transfer of fluid from the pressure equalization chamber 530 into the vial 500.

Reference is now made to FIGS. 18A & 18B are simplified respective pictorial and sectional illustrations of the vial adaptor assembly 100 of FIG. 1, shown in a tenth operative orientation, where the required amount of fluid 600 is retrieved from the vial 500 into the syringe 550 using the closed fluid transfer system, FIG. 18B being taken along lines B-B in FIG. 18A.

It is appreciated that all spatial relationships between the various components of the vial adaptor assembly 100, as described with reference to FIGS. 10A & 10B remain unchanged other than mentioned below, relationships between the adaptor assembly 100 and the vial 500 and between the syringe 550 and the syringe adaptor 560, as described with reference to FIGS. 17A & 17B remain unchanged other than mentioned below. Additional relationships between the vial adaptor assembly 100 and the vial 500 and between the syringe 550 and the syringe adaptor 560 now exist in this tenth operative orientation shown in FIGS. 18A & 18B, as described in detail hereinbelow.

It is seen in FIGS. 18A & 18B that the plunger rod 576 of the syringe 550 is further pulled outwardly by the user, such that the plunger rod 576 slides relative to barrel 570 of the syringe 550 and thus a portion of the fluid drug mixture 600 contained within the inner volume 504 of the vial 500 is aspirated through the needle element 110 of the vial adaptor assembly 100 into the needle 596 of the syringe adaptor 560 and further into the inner volume 572 of the syringe 550. The plunger rod 576 is shown in FIGS. 18A & 18B at the end of the aspiration process of the fluid drug mixture 600 into the barrel 570 of the syringe 550.

It is specifically seen in FIG. 18B that the fluid drug mixture 600 is aspirated from the inner volume 504 of the vial 500 through U-shaped opening 246 of the spike portion 182 and further through opening 296 of the needle element 110, which are submerged within the fluid drug mixture 600, and into the liquid pathway 292 of the needle element 110 and further flows through intermediate bore 392 of the syringe adaptor connector portion 104 into the inner volume of the needle 596 of the syringe adaptor 560 and further into barrel 570 of the syringe 550.

It is a particular feature of an embodiment of the present invention that due to the aspiration of fluid drug mixture 600 out of the inner volume 504 of the vial 500, the pressure within the vial 500 is decreased and thus urges passage of the second portion of fluid drug mixture 600, which accumulated within pressure equalization chamber 530 as shown and described with reference to FIG. 17B, from the pressure equalization chamber 530 formed between the deformable membrane 108 and the syringe adaptor connector portion 104 into the inner volume 504 of the vial 500. The deformable membrane 108 remains in the same orientation as shown in FIG. 17B.

It is a particular feature of an embodiment of the present invention that the volume of the pressure equalization chamber 530 is now empty of fluid drug mixture 600, due to the fact that the second portion of fluid drug mixture 600 that was previously accumulated in the pressure equalization chamber 530 is now transferred back into the inner volume 504 of the vial 500. It is specifically seen in FIG. 18B that the entire amount of fluid drug mixture 600 is forced out from the pressure equalization chamber 530 during aspiration of fluid by the syringe 550 due to the geometry of the syringe adaptor connector portion 104 forming the liquid medicament collecting and draining well 350 at the bottom of the pressure equalization chamber 530 and due to the pressure differential between the pressure equalization chamber 530 and the inner volume 504 of the vial 500.

It is specifically seen in FIG. 18B that the entire amount of fluid drug mixture 600 is drained from the pressure equalization chamber 530 and only air remains within the pressure equalization chamber 530. It is noted that after all of the fluid drug mixture 600 is drained from the pressure equalization chamber 530, the air contained within the pressure equalization chamber 530 is drawn into the inner volume 504 of the vial 500 as indicated by arrow 602, in order to continue the pressurizing process, optionally until the entire amount of fluid drug mixture 600 remaining in the vial 500 is drawn into the syringe 550.

The plunger rod 576 is shown at the process of the aspiration process in FIG. 18B, when the required amount of fluid drug mixture 600 was aspirated into the syringe 550, thus there is no fluid remaining within pressure equalization chamber 530, as shown in this operative orientation.

It is a particular feature of an embodiment of the present invention that increasing the pressure within the vial 500 urges transfer of fluid from the vial 500 into the pressure equalization chamber 530 and decreasing pressure within the vial 500 urges transfer of fluid from the pressure equalization chamber 530 into the vial 500.

Reference is now made to FIGS. 19A & 19B, which are simplified respective pictorial and sectional illustrations of the vial adaptor assembly 100 of FIG. 1, shown in an eleventh operative orientation, where the syringe 550 along with the syringe connector 560 are disconnected from the vial adaptor assembly 100 and the vial 500, FIG. 19B being taken along lines B-B in FIG. 19A.

It is appreciated that all spatial relationships between the various components of the vial adaptor assembly 100, as described with reference to FIGS. 10A & 10B remain unchanged other than mentioned below, relationships between the adaptor assembly 100 and the vial 500 and between the syringe 550 and the syringe adaptor 560, as described with reference to FIGS. 18A & 18B remain unchanged other than mentioned below. Additional relationships between the vial adaptor assembly 100 and the vial 500 and between the syringe 550 and the syringe adaptor 560 now exist in this eleventh operative orientation shown in FIGS. 19A & 19B, as described in detail hereinbelow.

It is seen in FIGS. 19A & 19B that the syringe 550 remains attached to the syringe adaptor 560. The syringe 550 and the syringe adaptor 560 are now disconnected from the vial adaptor assembly 100, similar to the operative orientation shown in FIGS. 11A & 11B.

It is appreciated that any fluid drug mixture 600 remaining within the inner volume 504 of the vial 500 is sealed therewithin by means of septum 114. Any fluid drug mixture 600 within the syringe 550 is sealed therewithin by means of a septum contained within the syringe adaptor 560, thus providing for a closed system for fluid transfer sealed from the outside environment.

It will be appreciated by persons skilled in the art that the present invention is not limited by what has been particularly shown and described hereinabove. Rather the scope of the present invention includes both combinations and sub-combinations of various features described hereinabove as well as variations and modifications thereof which are not in the prior art.

The invention claimed is:

1. A vial adaptor assembly, suitable for use with a vial containing a medicament and a syringe adaptor, which is in turn connectable to a syringe having a piston adapted for selectable displacement in a first direction for drawing fluid into said syringe and in a second direction for expelling fluid from said syringe, said vial adaptor assembly comprising:

a vial connector for non-removable connection with said vial containing said medicament;

a syringe adaptor connector for connection with said syringe adaptor;

a pressure equalization chamber having a variable volume, which is sealed from the outside environment during use;

a liquid pathway communicating between an interior of said vial containing a liquid medicament and an interior of said syringe when said syringe adaptor is connected to said syringe adaptor connector and said syringe is connected to said syringe adaptor and said vial connector is connected to said vial containing said liquid medicament; and a venting pathway communicating between said interior of said vial containing said liquid medicament and an interior of said pressure equalization chamber, when said vial connector is connected to said vial containing said liquid medicament, and wherein said pressure equalization chamber is configured with a liquid medicament collecting and draining well and wherein direct fluid communication is permitted between the pressure equalization chamber and the venting pathway via the liquid medicament collecting and draining well, and wherein said liquid medicament collecting and draining well is configured to permit liquid to enter and exit therefrom.

2. The vial adaptor assembly according to claim 1 and wherein: said vial adaptor assembly is generally axially symmetric about a longitudinal axis;

said liquid pathway extends generally along said longitudinal axis;

said venting pathway at least partially surrounds said liquid pathway; and said liquid medicament collecting and draining well is generally centered along said longitudinal axis.

3. The vial adaptor assembly according to claim 1 and wherein said pressure equalization chamber and said venting pathway are mutually configured such that, when said syringe adaptor is connected to said syringe adaptor connector and said syringe is connected to said syringe adaptor and said vial connector is connected to said vial containing said medicament, substantially all of any of said medicament that becomes located within said pressure equalization chamber is removed therefrom via said venting pathway and returned to said interior of said vial by displacement of said piston of said syringe in said first direction.

4. The vial adaptor assembly according to claim 1 and also comprising a deformable membrane, which is contained within a volume enclosed between said vial connector and said syringe adaptor connector and fixedly attached therebetween.

5. The vial adaptor assembly according to claim 4 and wherein said pressure equalization chamber is disposed between said syringe adaptor connector and said deformable membrane.

6. The vial adaptor assembly according to claim 1 and also comprising a needle element extending longitudinally along a longitudinal axis.

7. The vial adaptor assembly according to claim 1 and also comprising a septum element disposed within a portion of said syringe adaptor connector and configured for penetration thereof by a needle of a medical implement, which is adapted to engage said vial adaptor assembly.

8. The vial adaptor assembly according to claim 1, wherein said vial connector also comprises a plurality of circumferentially arranged snaps adapted for fixed engagement with said vial.

9. The vial adaptor assembly according to claim 1, wherein said vial connector also comprises a sheath having an upper portion and a spike portion.

10. The vial adaptor assembly according to claim 9 and wherein a longitudinal bore is formed through said sheath, and wherein said bore has a "drop" shape, having a wide portion and a narrow portion.

11. The vial adaptor assembly according to claim 4 and wherein said deformable membrane being a deformable sheet of material having a pre-defined shape, and which is adapted to change its shape in response to pressure that is applied thereon.

12. The vial adaptor assembly according to claim 9 and wherein said needle element has a cylindrical portion and a sharp tip and its inner volume defines said liquid pathway.

13. The vial adaptor assembly according to claim 12 and wherein said needle element has a fin extending radially outwardly from said cylindrical portion and an opening formed in the cylindrical portion and adapted to communicate with said liquid pathway.

14. The vial adaptor assembly according to claim 13 and wherein said opening is disposed adjacent said sharp tip of said needle element and is oriented at the same direction as said fin.

15. The vial adaptor assembly according to claim 1 and wherein said liquid medicament collecting and draining well has a tapered wall surface and a flat surface.

16. The vial adaptor assembly according to claim 4 and wherein said pressure equalization chamber is formed between said deformable membrane and said syringe adaptor connector.

17. The vial adaptor assembly according to claim 4 and wherein said deformable membrane is configured to change its shape in response to pressure that is exerted upon, thereby changing the volume of said pressure equalization chamber.

18. The vial adaptor assembly according to claim 13 and wherein said fin is disposed within a portion of said sheath and is adapted to orient said needle element such that said opening of said needle element and said opening of said spike portion are facing the same direction.

19. The vial adaptor assembly according to claim 13 and wherein a tip of said needle element protrudes axially longitudinally from said spike portion and together therewith forms a sharp tip, which is adapted for penetrating a septum of said vial containing said medicament.

20. The vial adaptor assembly according to claim 1 and wherein increasing the pressure within said vial urges transfer of fluid from said vial into said pressure equalization chamber; and decreasing the pressure within said vial urges transfer of fluid from said pressure equalization chamber into said vial.

21. The vial adapter assembly according to claim 1 wherein the said liquid medicament collecting and draining well is in communication with said interior of said vial.

* * * * *